(12) United States Patent
Forsgren et al.

(10) Patent No.: US 9,309,293 B2
(45) Date of Patent: Apr. 12, 2016

(54) **SURFACE EXPOSED *HAEMOPHILUS INFLUENZAE* PROTEIN (PROTEIN; PE)**

(71) Applicant: Olle Forsgren, Ekerö (SE)

(72) Inventors: Arne Forsgren, Falsterbo (SE); Kristian Riesbeck, Malmö (SE)

(73) Assignee: ARNE FORSGREN ET AL, Falsterbo (SE)

( * ) Notice: Subject to any disclaimer, the term of this patent is extended or adjusted under 35 U.S.C. 154(b) by 0 days.

(21) Appl. No.: 14/109,573

(22) Filed: Dec. 17, 2013

(65) Prior Publication Data

US 2014/0350220 A1 Nov. 27, 2014

Related U.S. Application Data

(63) Continuation of application No. 12/161,040, filed as application No. PCT/SE2007/000034 on Jan. 17, 2007, now Pat. No. 8,617,565.

(60) Provisional application No. 60/758,987, filed on Jan. 17, 2006.

(51) Int. Cl.
| | |
|---|---|
| *A61K 39/02* | (2006.01) |
| *A61K 48/00* | (2006.01) |
| *C12Q 1/68* | (2006.01) |
| *C12P 21/06* | (2006.01) |
| *C07K 14/235* | (2006.01) |
| *C12N 15/74* | (2006.01) |
| *C07K 14/285* | (2006.01) |
| *A61K 39/00* | (2006.01) |

(52) U.S. Cl.
CPC ............... *C07K 14/285* (2013.01); *A61K 39/00* (2013.01)

(58) Field of Classification Search
None
See application file for complete search history.

(56) References Cited

U.S. PATENT DOCUMENTS 5,721,115 A 2/1998 Krivan et al.

FOREIGN PATENT DOCUMENTS

| EP | 1 254 234 | 8/2001 |
| WO | WO 02/28889 | 4/2002 |
| WO | WO 2005/111066 A2 | 11/2005 |

OTHER PUBLICATIONS

International Search Report for International Application No. PCT/SE2007/000034, mailed Apr. 17, 2007.
Musacchio, A. et al. "Recombinant Opc meningococcal protein, folded in vitro, elicits bactericidal antibodies after immunization," *Vaccine* 15(6/7): 751-758 (1997).
U.S. Appl. No. 14/085,007, filed Nov. 20, 2013.

*Primary Examiner* — Robert A Zeman
(74) *Attorney, Agent, or Firm* — Finnegan, Henderson, Farabow, Garrett & Dunner LLP

(57) ABSTRACT

The present invention relates to a surface exposed protein (protein E; pE), a virulence factor, which can be detected in *Haemophilus influenzae*, having an amino acid sequence as described in SEQ ID NO: 1, an immunogenic fragment of said surface exposed protein, and a recombinant immunogenic protein (pE (A)) or truncated variants thereof based on said surface exposed protein. Nucleic acid sequences, vaccines, plasmids and phages, non human hosts, recombinant nucleic acid sequences, fusion proteins and fusion products are also described. A method of producing the said protein or truncated fragments thereof recombinantly is also disclosed.

4 Claims, 11 Drawing Sheets

A

+ IgD-λ

α-IgD pAb-FITC

B

C protein E

A

Predicted signal peptidase cleavage site

Native protein E    MKKIILTLSLGLLTACSAQIQKAEQNDVKL (SEQ ID NO: 31)

Recombinant protein E    MDIGINSDPKAKQNDVKL (SEQ ID NO: 32)

Vector sequence

B (SEQ ID NO: 33) MDIGINSDP — Vector sequence recombinant protein E (fragment A)  148 161  Histidine(6)-tag (SEQ ID NO: 12)

C

D  Stain

MinnA OMP    rec. pE 22-160

E  Western blot (IgD-λ)

MinnA OMP    rec. pE 22-160

SURFACE EXPOSED *HAEMOPHILUS INFLUENZAE* PROTEIN (PROTEIN; PE)

This application is a continuation of application Ser. No. 12/161,040, which has a §371 date of Nov. 18, 2008, and which is the U.S. national stage application of International Application No. PCT/SE2007/00034, filed on Jan. 17, 2007, which claims the benefit of priority of U.S. Provisional Application No. 60/758,987, filed on Jan. 17, 2006. All of these applications are herein incorporated by reference in their entireties.

FIELD OF THE INVENTION

The present invention relates to the surface exposed protein E, a virulence factor, which exists in all encapsulated and non-typable *Haemophilus influenzae*.

BACKGROUND OF THE INVENTION

Both *Haemophilus influenzae* type b (Hib) and non-typeable *H. influenzae* (NTHi) cause a variety of diseases in children and in adults. Hib causes bacterial meningitis and other invasive infections in children under the age of 4 years, whereas NTHi has been isolated from cases of otitis media, sinusitis, epiglottitis, tracheobronchitis, and pneumonia and may cause neonatal sepsis. There is currently no commercially available vaccine against NTHi, but a number of vaccines are in use against Hib. These vaccines consist of the Hib capsular polysaccharide, polyribosyl ribitol phosphate, conjugated to various protein carriers (meningococcol outer membrane complex, tetanus toxoid, nontoxic mutant diphtheria toxin, or diphtheria toxoid) to overcome the weak immune response to capsular polysaccharide in children younger than 18 months of age. *H. influenzae* outer membrane proteins (OMPs) are also considered to be carriers of polyribosyl ribitol phosphate since they are shown to be targets of host antibodies following Hib and NTHi infections. Antibodies to OMPs P1, P2, P4, P5, and P6 and a 98-kDa protein have been tested in in vivo protection and in vitro bactericidal assays against *H. influenzae* infections, with antibodies to P1, P4, and P6 showing biological activity against both homologous and heterologous *H. influenzae* strains. The lack of heterologous protection from antibodies to other OMPs is partly due to the antigenic diversity of these proteins among different *H. influenzae* strains. An ideal antigen must therefore be both exposed on the bacterial surface and antigenically well conserved. In this laboratory, a 42-kDa membrane protein (protein D) that is widely distributed and antigenically conserved among both Hib and NTHi strains has been isolated, cloned, sequenced, and shown to be a pathogenicity factor and a possible vaccine candidate (1-5).

Two decades ago, *Haemophilus influenzae* and *M. catarrhalis* were shown to display a strong affinity for both soluble and surface-bound human IgD (6). The IgD-binding seems to be paralleled by a similar interaction with surface-bound IgD at the cellular level, a phenomenon that explains the strong mitogenic effects on human lymphocytes by *H. influenzae* and *M. catarrhalis* (7-9). An IgD-binding outer membrane protein from *H. influenzae* (protein D) was isolated and cloned, and shown to be an important pathogenicity factor (1-5). However, protein D does not bind universally to all IgD myelomas(10).

SUMMARY OF THE INVENTION

In view of the fact that *H. influenzae* has been found to be such a leading cause of infections in the upper and lower airways, there is a current need to develop vaccines that can be used against *H. influenzae*.

The aim of the present invention has therefore been to find out in which way *H. influenzae* interacts with cells in the body and interacts with the immune system, and be able to provide a new type of vaccine.

According to one aspect, the present invention provides a surface exposed protein, which can be detected in *Haemophilus influenzae*, having an amino acid sequence according to SEQ ID NO: 1, or a fragment, homologue, functional equivalent, derivative, degenerate or hydroxylation, sulphonation or glycosylation product or other secondary processing product thereof.

According to another aspect the present invention provides an immunogenic fragment of said surface exposed protein, which fragment can be detected in *Haemophilus influenzae*, or naturally occurring or artificially modified variants thereof.

According to a further aspect the present invention provides a recombinant immunogenic protein based on the surface exposed protein mentioned above, wherein the amino acids in position 1 to 21 of SEQ ID NO: 1 have been deleted or replaced by one or more amino acids. In one embodiment the amino acids in position 1 to 21 of SEQ ID NO: 1 have been replaced by a sequence of 0 to 21 optional amino acids. In another embodiment the reimmunogenic protein have an amino acid sequence according to SEQ ID NO: 2, or a fragment, homologue, functional equivalent, derivative, degenerate or hydroxy sulphonation or glycosylation product or other secondary processing product thereof.

According to a further aspect the present invention provides a peptide having an amino acid sequence according to SEQ ID NO: 3, or a fragment, homologue, functional equivalent, derivative, degenerate or hydroxylation, sulphonation or glycosylation product or other secondary processing product thereof.

According to still a further aspect the present invention provides a peptide having an amino acid sequence according to SEQ ID NO: 4, or a fragment, homologue, functional equivalent, derivative, degenerate or hydroxylation, sulphonation or glycosylation product or other secondary processing product thereof.

According to yet a further aspect the present invention provides a peptide having an amino acid sequence according to SEQ ID NO: 5, or a fragment, homologue, functional equivalent, derivative, degenerate or hydroxylation, sulphonation or glycosylation product or other secondary processing product thereof.

According to a further aspect the present invention provides a peptide having an amino acid sequence according to SEQ ID NO: 6, or a fragment, homologue, functional equivalent, derivative, degenerate or hydroxylation, sulphonation or glycosylation product or other secondary processing product thereof.

According to still a further aspect the present invention provides a peptide having an amino acid sequence according to SEQ ID NO: 7, or a fragment, homologue, functional equivalent, derivative, degenerate or hydroxylation, sulphonation or glycosylation product or other secondary processing product thereof.

According to yet a further aspect the present invention provides a peptide having an amino acid sequence according to SEQ ID NO: 8, or a fragment, homologue, functional equivalent, derivative, degenerate or hydroxylation, sulphonation or glycosylation product or other secondary processing product thereof.

According to a further aspect the present invention provides a peptide having an amino acid sequence according to SEQ ID NO: 9, or a fragment, homologue, funcequivalent, derivative, degenerate or hydroxylation, sulphonation or glycosylation product or other secondary processing product thereof.

According to another aspect the present invention provides a peptide having an amino acid sequence according to SEQ ID NO: 10, or a fragment, homologue, functional equivalent, derivative, degenerate or hydroxylation, sulphonation or glycosylation product or other secondary processing product thereof.

According to another aspect the present invention provides the use of at least one protein, fragment or peptide as described above for the manufacturing of a medicament for the prophylaxis or treatment of an infection. In one embodiment the infection is caused by *Haemophilus influenzae*, and in another embodiment the *Haemophilus influenzae* is encapsulated or non-typable. In still another embodiment, said use is for the prophylaxis or treatment of otitis media, sinusitis or lower respiratory tract infections, in children as well as adults with, for example, chronic obstructive pulmonary disease (COPD).

According to one aspect, the present invention provides a medicament comprising at least one protein, fragment or peptide as described above and one or more pharmaceutically acceptable adjuvants, vehicles, excipients, binders, carriers, preservatives, buffering agents, emulsifying agents, wetting agents, or transfection facilitating compounds.

According to another aspect, the present invention provides a vaccine composition comprising at least one protein, fragment or peptide as described above. In one embodiment, said vaccine composition comprises at least one di-, tri- or multimer of said protein, fragment or peptide. In another embodiment, the vaccine composition, further comprises one or more pharmaceutically acceptable adjuvants, vehicles, excipients, binders, carriers, preservatives, buffering agents, emulsifying agents, wetting agents, or transfection facilitating compounds. In still another embodiment, said vaccine composition comprises at least one further vaccine, and in yet another embodiment it comprises an immunogenic portion of another molecule, wherein the immunogenic portion of another molecule can be chosen from the group comprising Protein D of *H. influenzae* (EP 594 610), MID of *Moraxella catarrhalis* (WO 03/004651, WO 97/41731 and WO96/34960), UspA1 or UspA2 of *Moraxella catarrhalis* (WO93/03761), and outer membrane protein or carbohydrate capsule, of any respiratory tract pathogen, or DNA oligonucleotides, such as CpG motif.

In one aspect the present invention relates to a nucleic acid sequence encoding a protein, fragment or peptide as described above, as well as homologues, polymorphisms, degenerates and splice variants thereof. In one embodiment, said nucleic acid sequence is fused to at least another gene.

In another aspect the present invention relates to a plasmid or phage comprising a nucleic acid sequence as described above.

In yet another embodiment the present invention relates to a non human host comprising at least one plasmid as described above and capable of producing a protein, fragment or peptide as discussed above, as well as homologues, polymorphisms, degenerates and splice variants thereof, which host is chosen among bacteria, yeast and plants. In one embodiment, said host is *E. coli*.

In still another aspect, the present invention provides a fusion protein or polypeptide, in which a protein, fragment or peptide as described above is combined with at least another protein by the use of a recombinant nucleic acid sequence as discussed above. In one embodiment, said fusion protein is a di-, tri or multimer of a protein, fragment or peptide as discussed above.

In one aspect, the present invention relates to a fusion product, in which a protein, fragment or peptide as described above is covalently, or by any other means, bound to a protein, carbohydrate or matrix.

In yet another aspect the present invention relates to a method of isolation of a protein, fragment or peptide as described above, said method comprising the steps:

a) growing *Haemophilus influenzae* or *E. coli* comprising the DNA coding for said protein, fragment or peptide, harvesting the bacteria and isolating outer membranes or inclusion bodies;

b) solubilizing the inclusion bodies with a strong solvatising agent;

c) adding a renaturating agent; and d) dialyzing the resulting suspension against a buffer with a pH of from 8 to 10.

In one embodiment of said method the solvalising agent is guanidium hydrochloride, and in another embodiment the renaturating agent is arginin.

In another aspect the present invention relates to a medicament or a vaccine composition as discussed above, comprising said fusion protein or polypeptide, or said fusion product.

In one aspect the present invention relates to a method of preventing or treating an infection in an individual comprising administering a pharmaceutically effective amount of a medicament or a vaccine composition as described above. In one embodiment said infection is caused by *Haemophilus influenzae*, both encapsulated or non-typable, and in yet another embodiment the infection is chosen from the group consisting of otitis media, sinusitis or lower respiratory tract infections.

The present invention relates to Protein E, in particular Protein E polypeptides and Protein E polynucleotides, recombinant materials and methods for their production. In another aspect, the invention relates to methods for using such polypeptides and polynucleotides, including prevention and treatment of microbial diseases, amongst others. In a further aspect, the invention relates to diagnostic assays for detecting diseases associated with microbial infections and conditions associated with such infections, such as assays for detecting expression or activity of Protein E polynucleotides or polypeptides.

Various changes and modifications within the spirit and scope of the disclosed invention will become readily apparent to those skilled in the art from reading the following descriptions and from reading the other parts of the present disclosure.

DESCRIPTION OF THE FIGURES

Figure 11:
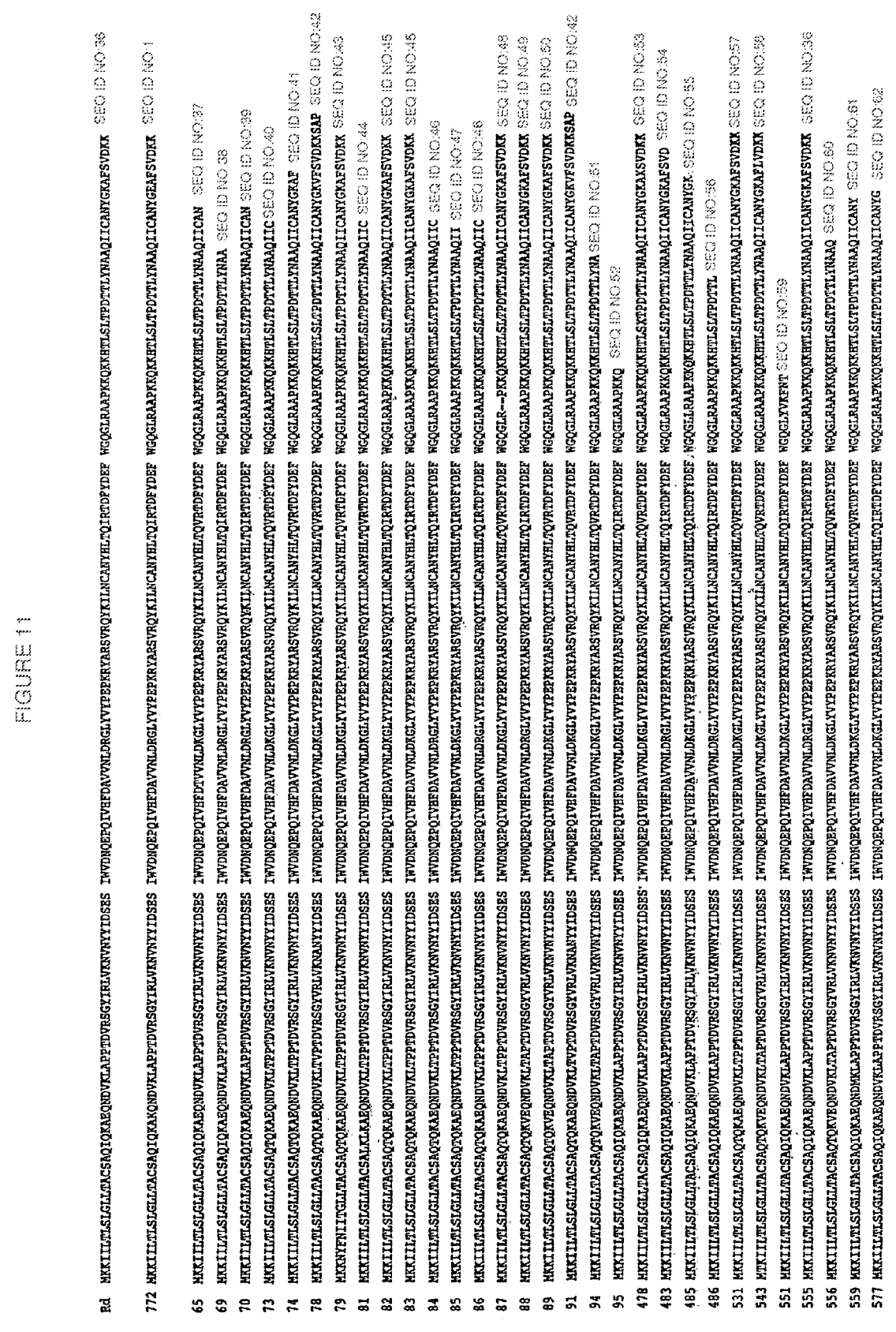

FIG. 11 pE is extraordinary conserved within different *haemophilus* strains. The pe gene was sequenced in encapsulated *H. influenzae* type a (n=2), b (n=2), c (n=2), d (n=1), e (n=2), and f (n=3), NTHi (n=8), *H. influenzae* biovar *aegypticus* (n=6) and *H. aegypticus* (n=5), using flanking primers. Rd designates *H. influenzae* strain Rd (Hi0178) and 772 the NTHi strain 772. The numbers 65 to 577 correspond to the strains outlined in Table 1. The 32 listed sequences correlate to SEQ ID NO: 36, 1, 37, 38, 39, 40, 41, 42, 43, 44, 45, 45, 46, 47, 46, 48, 49, 50, 42, 51, 52, 53, 54, 55, 56, 57, 58, 59, 36, 60, 61 and 62, respectively, in order of appearance from top to bottom).

DESCRIPTION OF THE INVENTION

Figure 1:
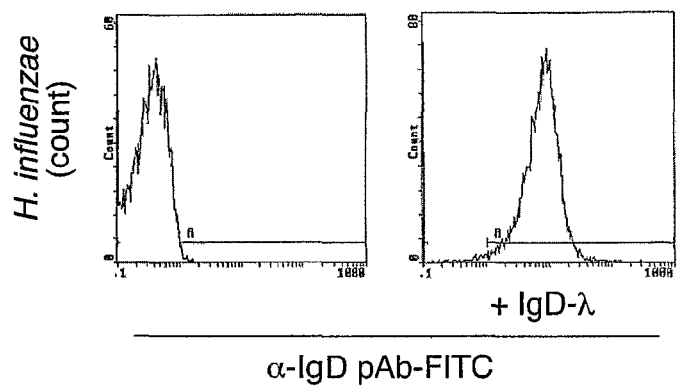
FIG. 1. The 16.3 kDa *Haemophilus influenzae* protein E is detected by an IgD($\lambda$) myeloma protein. In A, flow cytometry analysis of pE expression in *H. influenzae* 772 is demonstrated. SDS-PAGE and Western blot (B) and 2-dimensional SDS-polyacrylamide gel electrophoresis analyses (C) of Empigen®-treated outer membrane proteins of *H. influenzae* MinnA is shown. Outer membrane protein extracts are shown before (B) and after separation on Q-Sepharose (C). The arrow in panel C indicates the predicted localization for pE based upon a Western blot (using IgD($\lambda$) as a probe) of a corresponding gel. In A, bacteria were loaded with IgD($\lambda$) myeloma protein followed by incubation with rabbit FITC-conjugated anti-IgD pAb and flow cytometry analysis. In B, a Coomassie blue stained SDS-gel (stain) and Western blot probed with human myeloma IgD(λ) followed by incubation with horseradish peroxidase-conjugated goat anti-human IgD polyclonal antibodies are shown. Samples were boiled in the presence of 2-mercaptoethanol for 10 min prior to loading.
Figure 1:
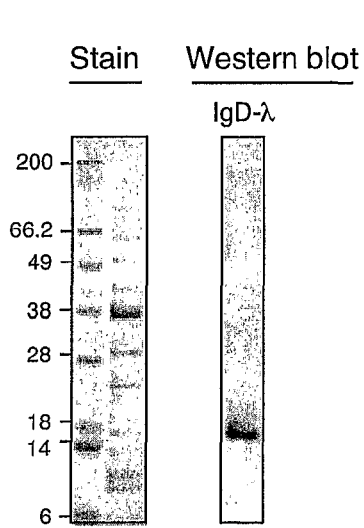
Figure 1:
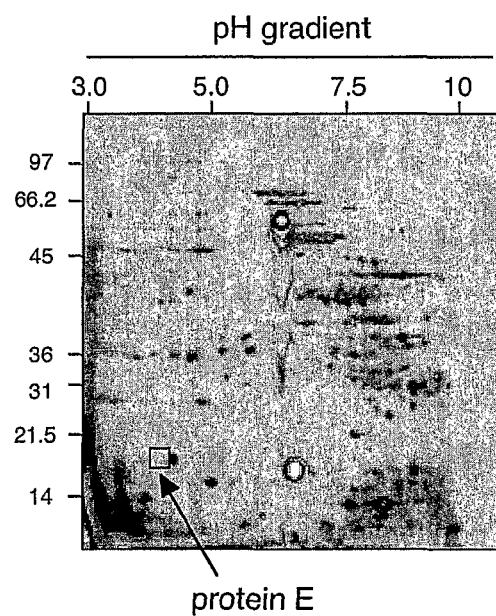

Before explaining the present invention in detail, it is important to understand that the invention is not limited in this application to the details of the embodiments and steps described herein. The examples mentioned are illustrative of the invention but do not limit it in any way. The invention is capable of other embodiments and of being practiced or carried out in a variety of ways. It is to be understood that the phraseology and terminology employed herein is for the purpose of description and not of limitation.

The present application describes the cloning and expression of a novel *H. influenzae* outer membrane protein designated protein E (pE). The protein was discovered using a human IgD (λ) myeloma serum with specific affinity for pE.

To maximize the yield of recombinant pE, a truncated pE fragment consisting of amino acid residues lysine22 to lysine160 was manufactured. The N-terminal signal peptide including the amino acid glutamine21 was thus removed and replaced with the leader peptide in addition to nine residues originating from the vector pET26(+). The truncated pE (i.e., pE22-160) was designated pE(A).

The present invention comprises the *Haemophilus* outer membrane protein pE and the pE-derived peptides pE22-60, pE22-95, pE22-125, pE41-68, pE56-125, pE56-160, pE86-160, pE115-160, and di-, tri- or oligomers thereof. In particular, sequences of pE or the derived peptides that are surface exposed are given a higher priority Thus, the vaccine compositions according to the present invention comprises as immunogenic components a surface exposed protein, a recombinant immunogenic protein based on said surface exposed protein, a recombinant immunogenic protein having an amino acid sequence according to SEQ ID NO: 2, and/or a peptide having an amino acid sequence according to SEQ ID NO: 3-10, or a fragment, homo functional equivalent, derivative, degenerate or hydroxylation, sulphonation, or glycosylation product or other secondary processing product thereof. The vaccine compositions may also comprise a fusion protein or polypeptide, or a fusion product according to the present invention as immunogenic components. The immunogenic components are capable of eliciting an antibody or other immune response to *Haemophilus influenzae*, wherein the antibodies elicited inhibit the pathogenesis of *Haemophilus influenzae* bacterium to the cells of the subject. An "immunogenic dose" of a vaccine composition according to the invention is one that generate, after administration, a detectable humoral and/or cellular immune response in comparison to a standard immune response before administration.

The nucleic sequences used in the vaccine compositions of the present invention to generate the antigens may be inserted into any of a wide variety of expression vectors by a variety of procedures. Such procedures are deemed to be known by those skilled in the art.

Vaccine compositions are easily accomplished using well known methods and techniques, and can be administered in a variety of ways, preferably parenterally or intranasally. Formulations suitable for parenteral or intranasal administration include aqueous and non-aqueous sterile injection solutions which may contain anti-oxidants, buffers, bacteriostats and solutes that makes the formulation isotonic with the bodily fluid of the subject in question; and aqueous and non-aqueous sterile suspensions which may include suspending agents or thickening agents. The active immunogenic ingredient is often mixed with excipients which are pharmaceutically acceptable, e g water, saline, dextrose, glycerol, ethanol, or the like. In addition, the vaccine composition can also contain minor amounts of auxiliary substances such as wetting or emulsifying agents, pH buffering agents, binders, carriers or preservatives.

The vaccine compositions may also include adjuvants for enhancing the immunogenicity of the composition, such as Freund's Adjuvants and other systems known in the art. The immunogenic components of the vaccine compositions, ie the proteins, fragments, peptides, fusion proteins or polypeptides, or fusion products of the present invention, may be formulated into the vaccine as neutral or salt forms.

The dosage of the vaccine compositions will depend on the specific activity of the vaccine and can be readily determined by routine experimentation. The vaccine compositions are administered in such an amount as will be therapeutically effective and immunogenic, and the quantity depends on the subject.

The invention relates to Protein E polypeptides and polynucleotides as described in greater detail below. In particular, the invention relates to polypeptides and polynucleotides of Protein E of non typeable *H. Influenzae*. The Protein E polypeptides have a signal sequence and are exposed at the surface of the bacteria. The signal peptide is located from residue 1 to residue 20 of Protein E polypeptide.

A reference to "Protein E" herein is a reference to any of the peptides, immunogenic fragments, fusions, polypeptides or proteins of the invention discussed herein (such as SEQ ID NO: 1 with or without the signal sequence). A "polynucleotide encoding Protein D" refers to any polynucleotide sequence encoding any of the peptides, immunogenic fragments, fusions, polypeptides or proteins of the invention discussed herein.

The term "comprising" herein alternatively may be substituted with the term "consisting of".

The invention relates especially to Protein E polynucleotides and encoded polypeptides listed herein.

It is understood that sequences recited in the Sequence Listing below as "DNA" represent an exemplification of one embodiment of the invention, since those of ordinary skill will recognize that such sequences can be usefully employed in polynucleotides in general, including ribopolynucleotides.

The sequences of the Protein E polynucleotides are set out in SEQ ID NO: 11 (from ntHi strain 772).

The sequences of the Protein E encoded polypeptides are set out in SEQ ID NO:1 (from ntHi strain 772), 2, 3, 4, 5, 6, 7, 8, 9, 10.

Polypeptides

In one aspect of the invention there are provided polypeptides of *H. influenzae* (in particular non typeable *H. influenzae*) referred to herein as "Protein E" and "Protein E polypeptides" as well as biologically, diagnostically, prophylactically, clinically or therapeutically useful variants thereof, and compositions comprising the same.

The present invention further provides for:

(a) an isolated polypeptide which comprises an amino acid sequence which has at least 85% identity, preferably at least 90% identity, more preferably at least 95% identity, most preferably at least 97-99% or exact identity, to that of any sequence of SEQ ID NO: 1-10;

(b) a polypeptide encoded by an isolated polynucleotide comprising a polynucleotide sequence which has at least 85% identity, preferably at least 90% identity, more preferably at least 95% identity, even more preferably at least 97-99% or exact identity to any sequence of SEQ ID NO: 11 over the entire length of the selected sequence of SEQ ID NO: 11; or (c) a polypeptide encoded by an isolated polynucleotide comprising a polynucleotide sequence encoding a polypeptide which has at least 85% identity, preferably at least 90% identity, more preferably at least 95% identity, even more preferably at least 97-99% or exact identity, to the amino acid sequence of any sequence of SEQ ID NO: 1-10.

The Protein E polypeptides provided in SEQ ID NO: 1-10 are the Protein E polypeptides from non typeable *H. influenzae* strains. Further Protein E sequences have been ascertained from *H. influenzae* strains listed in Table 1.

The invention also provides an immunogenic fragment of a Protein E polypeptide, that is, a contiguous portion of the Protein E polypeptide which has the same or substantially the same immunogenic activity as the polypeptide comprising the corresponding amino acid sequence selected from SEQ ID NO: 1-10; That is to say, the fragment (if necessary when coupled to a carrier) is capable of raising an immune response which recognises the Protein E polypeptide. Alternatively, or in addition, the immunogenic fragment may retain an IgD binding function of the full length protein (as described in the Example section, for instance the capability to bind IgD(λ) from The Binding Site (Birmingham, England). Such an immunogenic fragment may include, for example, the Protein E polypeptide lacking an N-terminal leader sequence, and/or a transmembrane domain and/or a C-terminal anchor domain. In a preferred aspect the immunogenic fragment of Protein E according to the invention comprises substantially all of the extracellular domain of a polypeptide which has at least 85% identity, preferably at least 90% identity, more preferably at least 95% identity, most preferably at least 97-99% identity, to that a sequence selected from SEQ ID NO: 1-10 over the entire length of said sequence.

A fragment is a polypeptide having an amino acid sequence that is entirely the same as part but not all of any amino acid sequence of any polypeptide of the invention. As with Protein E polypeptides, fragments may be "free-standing," or comprised within a larger polypeptide of which they form a part or region, most preferably as a single continuous region in a single larger polypeptide. A fragment may therefore be shorter than the full-length native sequence, or, if comprised within a larger polypeptide, may be a full length native sequence or a longer fusion protein.

Preferred fragments include, for example, truncation polypeptides having a portion of an amino acid sequence selected from SEQ ID NO: 1-10 or of variants thereof, such as a continuous series of residues that includes an amino- and/or carboxyl-terminal amino acid sequence. Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from an amino acid sequence selected from SEQ ID NO: 1-10 or an isolated polypeptide comprising an amino acid sequence having at least 15, 20, 30, 40, 50 or 100 contiguous amino acids truncated or deleted from an amino acid sequence selected from SEQ ID NO: 1-10.

Still further preferred fragments are those which comprise a B-cell epitope, for example those fragments/peptides described in Example 10.

Fragments of the polypeptides of the invention may be employed for producing the corresponding full-length polypeptide by peptide synthesis; therefore, these fragments may be employed as intermediates for producing the full-length polypeptides of the invention.

Particularly preferred are variants in which several, 5-10, 1-5, 1-3, 1-2 or 1 amino acids are substituted, deleted, or added in any combination.

The polypeptides, or immunogenic fragments, of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa.

Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenzae* (EP 594610) and the non-structural protein from influenza virus, NS1 (hemagglutinin). Another fusion partner is the protein known as Omp26 (WO 97/01638). Another fusion partner is the protein known as LytA. Preferably the C terminal portion of the molecule is used. LytA is derived from *Streptococcus pneumoniae* which synthesize an N-acetyl-L-alanine amidase, amidase LytA, (coded by the lytA gene {Gene, 43 (1986) page 265-272}) an autolysin that specifically degrades certain bonds in the peptidoglycan backbone. The C-terminal domain of the LytA protein is responsible for the affinity to the choline or to some choline analogues such as DEAE. This property has been exploited for the development of *E. coli* C-LytA expressing plasmids useful for expression of fusion proteins. Purification of hybrid proteins containing the C-LytA fragment at its amino terminus has been described {Biotechnology: 10, (1992) page 795-798}. It is possible to use the repeat portion of the LytA molecule found in the C terminal end starting at residue 178, for example residues 188-305.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

It is most preferred that a polypeptide of the invention is derived from non typeable *H. influenzae*, however, it may preferably be obtained from other organisms of the same taxonomic genus. A polypeptide of the invention may also be obtained, for example, from organisms of the same taxonomic family or order.

Polynucleotides

It is an object of the invention to provide polynucleotides that encode Protein E polypeptides, particularly polynucleotides that encode the polypeptides herein designated Protein E.

In a particularly preferred embodiment of the invention the polynucleotides comprise a region encoding Protein E polypeptides comprising sequences set out in SEQ ID NO: 11 which include full length gene, or a variant thereof.

The Protein E polynucleotides provided in SEQ ID NO: 11 are the Protein E polynucleotides from non typeable *H. influenzae* strain 772. Other sequences have been determined of genes encoding protein E from *H. influenzae* strains listed in Table 1.

As a further aspect of the invention there are provided isolated nucleic acid molecules encoding and/or expressing Protein E polypeptides and polynucleotides, particularly non typeable *H. influenzae* Protein E polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a Protein E polypeptide having a deduced amino acid sequence of SEQ ID NO: 1-10 and polynucleotides closely related thereto and variants thereof.

In another particularly preferred embodiment of the invention relates to Protein E polypeptide from non typeable *H. influenzae* comprising or consisting of an amino acid sequence selected from SEQ ID NO: 1-10 or a variant thereof.

Using the information provided herein, such as a polynucleotide sequences set out in SEQ ID NO: 11, a polynucleotide of the invention encoding Protein E polypeptides may be obtained using standard cloning and screening methods, such as those for cloning and sequencing chromosomal DNA fragments from bacteria using non typeable *H. influenzae* strain_3224A (or 772) cells as starting material, followed by obtaining a full length clone. For example, to obtain a polynucleotide sequence of the invention, such as a polynucleotide sequence given in SEQ ID NO: 11, typically a library of clones of chromosomal DNA of non typeable *H. influenzae* strain 3224A (or 772) in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, the polynucleotide set out in SEQ ID NO: 11 was discovered in a DNA library derived from non typeable *H. influenzae*.

Moreover, each DNA sequence set out in SEQ ID NO: 11 contains an open reading frame encoding a protein having about the number of amino acid residues set forth in SEQ ID NO: 1 with a deduced molecular weight that can be calculated using amino acid residue molecular weight values well known to those skilled in the art.

The polynucleotides of SEQ ID NO: 11, between the start codon and the stop codon, encode respectively the polypeptide of SEQ ID NO: 1.

In a further aspect, the present invention provides for an isolated polynucleotide comprising or consisting of:
(a) a polynucleotide sequence which has at least 85% identity, preferably at least 90% identity, more preferably at least 95% identity, even more preferably at least 97-99% or exact identity, to any polynucleotide sequence from SEQ ID NO: 11 over the entire length of the polynucleotide sequence from SEQ ID NO: 11; or
(b) a polynucleotide sequence encoding a polypeptide which has at least 85% identity, preferably at least 90% identity, more preferably at least 95% identity, even more preferably at least 97-99% or 100% exact identity, to any amino acid sequence selected from SEQ ID NO: 1-10 (or fragment thereof), over the entire length of the amino acid sequence from SEQ ID NO: 1-10 (or fragment).

A polynucleotide encoding a polypeptide of the present invention, including homologs and orthologs from species other than non typeable *H. influenzae*, may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising any sequence selected from SEQ ID NO: 11 or a fragment thereof; and isolating a full-length gene and/or genomic clones containing said polynucleotide sequence.

The invention provides a polynucleotide sequence identical over its entire length to a coding sequence (open reading frame) set out in SEQ ID NO: 11. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide (SEQ ID NO: 12), as provided in the pQE vector (Qiagen, Inc.) and described in Gentz et al., *Proc. Natl. Acad. Sci., USA* 86: 821-824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding the Protein E polypeptide of SEQ ID NO: 1-10 may be identical to the corresponding polynucleotide encoding sequence of SEQ ID NO: 11 (or comprised within SEQ ID NO: 11). Alternatively it may be any sequence, which as a result of the redundancy (degeneracy) of the genetic code, also encodes a polypeptide of SEQ ID NO: 1-10.

The term "polynucleotide encoding a polypeptide" as used herein encompasses polynucleotides that include a sequence encoding a polypeptide of the invention, particularly a bacterial polypeptide and more particularly a polypeptide of the non typeable *H. influenzae* Protein E having an amino acid sequence set out in any of the sequences of SEQ ID NO: 1-10 or fragments thereof. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of any of the sequences of SEQ ID NO: 1-10. Fragments of polynucleotides of the invention may be used, for example, to synthesize full-length polynucleotides of the invention.

Preferred fragments are those polynucleotides which encode a B-cell epitope, for example the fragments/peptides described in Example 10, and recombinant, chimeric genes comprising said polynucleotide fragments.

Further particularly preferred embodiments are polynucleotides encoding Protein E variants, that have the amino acid sequence of Protein E polypeptide of any sequence from SEQ ID NO: 1-10 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of Protein E polypeptide (for instance those properties described in the Example section herein).

Further preferred embodiments of the invention are polynucleotides that are at least 85% identical over their entire length to polynucleotides encoding Protein E polypeptides having an amino acid sequence set out in any of the sequences of SEQ ID NO: 1-10, and polynucleotides that are complementary to such polynucleotides. Alternatively, most highly preferred are polynucleotides that comprise a region that is at least 90% identical over its entire length to polynucleotides encoding Protein E polypeptides and polynucleotides complementary thereto. In this regard, polynucleotides at least 95% identical over their entire length to the same are particularly preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA sequence selected from SEQ ID NO: 11 (for instance those activities described in the Example section herein).

In accordance with certain preferred embodiments of this invention there are provided polynucleotides that hybridize, particularly under stringent conditions, to Protein E polynucleotide sequences, such as those polynucleotides of SEQ ID NO: 11.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in any of the sequences of SEQ ID NO: 11 under stringent hybridization conditions with a probe having the sequence of said polynucleotide sequence set forth in the corresponding sequence of SEQ ID NO: 11 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding Protein E and to isolate cDNA and genomic clones of other genes that have a high identity, particularly high sequence identity, to the Protein E genes. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of Protein E genes may be isolated by screening using a DNA sequence provided in SEQ ID NO: 11 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., PNAS USA 85: 8998-9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ ID NO: 11 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In accordance with an aspect of the invention, there is provided the use of a polynucleotide of the invention for therapeutic or prophylactic purposes, in particular genetic immunization.

The use of a polynucleotide of the invention in genetic immunization will preferably employ a suitable delivery method such as direct injection of plasmid DNA into muscles (Wolff et al., *Hum Mol Genet* (1992) 1: 363, Manthorpe et al., *Hum. Gene Ther*. (1983) 4: 419), delivery of DNA complexed with specific protein carriers (Wu et al., *J Biol Chem*. (1989) 264: 16985), coprecipitation of DNA with calcium phosphate (Benvenisty & Reshef, *PNAS USA,* (1986) 83: 9551), encapsulation of DNA in various forms of liposomes (Kaneda et al., *Science* (1989) 243: 375), particle bombardment (Tang et al., *Nature* (1992) 356:152, Eisenbraun et al., *DNA Cell Biol* (1993) 12: 791) and in vivo infection using cloned retroviral vectors (Seeger et al., *PNAS USA* (1984) 81: 5849).

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL,* 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, conjugation, transduction, scrape loading, ballistic introduction and infection.

Representative examples of appropriate hosts include bacterial cells, such as cells of streptococci, staphylococci, enterococci, *E. coli, streptomyces,* cyanobacteria, *Bacillus subtilis, Neisseria meningitidis, Haemophilus influenzae* and *Moraxella catarrhalis*; fungal cells, such as cells of a yeast, *Kluveromyces, Saccharomyces, Pichia,* a basidiomycete, *Candida albicans* and *Aspergillus*; insect cells such as cells of *Drosophila* S2 and *Spodoptera* Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses, retroviruses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g; vaccinia, fowlpox, canarypox), alphaviruses (Sindbis virus, Semliki Forest Virus, Venezuelian Equine Encephalitis Virus), adenoviruses, adeno-associated virus, picornaviruses (poliovirus, rhinovirus), herpesviruses (varicella zoster virus, etc), *Listeria, Salmonella, Shigella*, BCG, streptococci. These viruses and bacteria can be virulent, or attenuated in various ways in order to obtain live vaccines. Such live vaccines also form part of the invention.

Diagnostic, Prognostic, Serotyping and Mutation Assays

This invention is also related to the use of Protein E polynucleotides and polypeptides of the invention for use as diagnostic reagents. Detection of Protein E polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the Protein E genes or proteins, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled Protein E polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science,* 230: 1242 (1985). Sequence changes at specific locations also may be revealed by nuclease protection assays, such as RNase, V1 and S1 protection assay or a chemical cleavage method. See, for example, Cotton et al., *Proc. Natl. Acad. Sci., USA,* 85: 4397-4401 (1985).

In another embodiment, an array of oligonucleotides probes comprising Protein E nucleotide sequences or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., Science, 274: 610 (1996)).

Thus in another aspect, the present invention relates to a diagnostic kit which comprises:

(a) a polynucleotide of the present invention, preferably any of the nucleotide sequences of SEQ ID NO: 11, or a fragment thereof;

(b) a nucleotide sequence complementary to that of (a);

(c) a polypeptide of the present invention, preferably any of the polypeptides of SEQ ID NO: 1-10 or a fragment thereof; or (d) an antibody to a polypeptide of the present invention, preferably to any of the polypeptides of SEQ ID NO: 1-10. It will be appreciated that in any such kit, (a), (b), (c) or (d) may comprise a substantial component. Such a kit will be of use in diagnosing a disease or susceptibility to a Disease, among others.

This invention also relates to the use of polynucleotides of the present invention as diagnostic reagents. Detection of a mutated form of a polynucleotide of the invention, preferably any sequence of SEQ ID NO: 11, which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding Protein E polypeptides can be used to identify and analyze mutations.

The invention further provides primers with 1, 2, 3 or 4 nucleotides removed from the 5' and/or the 3' end. These primers may be used for, among other things, amplifying Protein E DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing, disease, preferably bacterial infections, more preferably infections caused by non typeable *H. influenzae*, comprising determining from a sample derived from an individual, such as a bodily material, an increased level of expression of polynucleotide having a sequence of any of the sequences of SEQ ID NO: 11. Increased or decreased expression of Protein E polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of Protein E polypeptides compared to normal control tissue samples may be used to detect the presence of an infection, for example. Assay techniques that can be used to determine levels of Protein E polypeptides, in a sample derived from a host, such as a bodily material, are well-known to those of skill in the art. Such assay methods include radio-immunoassays, competitive-binding assays, Western Blot analysis, antibody sandwich assays, antibody detection and ELISA assays.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probes obtained or derived from a bodily sample, to determine the presence of a particular polynucleotide sequence or related sequence in an individual. Such a presence may indicate the presence of a pathogen, particularly non-typeable *H. influenzae*, and may be useful in diagnosing and/or prognosing disease or a course of disease. A grid comprising a number of variants of any polynucleotide sequence of SEQ ID NO: 11 is preferred. Also preferred is a number of variants of a polynucleotide sequence encoding any polypeptide sequence of SEQ ID NO: 1-10.

Antibodies

The polypeptides and polynucleotides of the invention or variants thereof, or cells expressing the same can be used as immunogens to produce antibodies immunospecific for such polypeptides or polynucleotides respectively. Alternatively, mimotopes, particularly peptide mimotopes, of epitopes within the polypeptide sequence may also be used as immunogens to produce antibodies immunospecific for the polypeptide of the invention. The term "immunospecific" means that the antibodies have substantially greater affinity for the polypeptides of the invention than their affinity for other related polypeptides in the prior art.

In certain preferred embodiments of the invention there are provided antibodies against Protein E polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495-497 (1975); Kozbor et al., *Immunology Today* 4: 72 (1983); Cole et al., pg. 77-96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms or animals, such as other mammals, may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti-Protein E or from naive libraries (McCafferty, et al., (1990), Nature 348, 552-554; Marks, et al., (1992) *Biotechnology* 10, 779-783). The affinity of these antibodies can also be improved by, for example, chain shuffling (Clackson et al., (1991) *Nature* 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against Protein E polypeptides or Protein E polynucleotides may be employed to treat infections, particularly bacterial infections.

Polypeptide variants include antigenically, epitopically or immunologically equivalent variants form a particular aspect of this invention.

Preferably, the antibody or variant thereof is modified to make it less immunogenic in the individual. For example, if the individual is human the antibody may most preferably be "humanized," where the complimentarity determining region or regions of the hybridoma-derived antibody has been transplanted into a human monoclonal antibody, for example as described in Jones et al. (1986), *Nature* 321, 522-525 or Tempest et al., (1991) *Biotechnology* 9, 266-273.

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1 (2): Chapter 5 (1991).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring Protein E polypeptides and/or polynucleotides activity in the mixture, and comparing the Protein E polypeptides and/or polynucleotides activity of the mixture to a standard. Fusion proteins, such as those made from Fc portion and Protein E polypeptides, as hereinbefore described, can also be used for high-throughput screening assays to identify antagonists of the polypeptide of the present invention, as well as of phylogenetically and and/or functionally related polypeptides (see D. Bennett et al., J Mol Recognition, 8:52-58 (1995); and K. Johanson et al., J Biol Chem, 270(16):9459-9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of Protein E polypeptides or polynucleotides, particularly those compounds that are bacteriostatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising Protein E polypeptides and a labeled substrate or ligand of such polypeptide is incubated in the absence or the presence of a candidate molecule that may be a Protein E agonist or antagonist. The ability of the candidate molecule to agonize or antagonize the Protein E polypeptide is reflected in decreased binding of the labeled ligand or decreased production of product from such substrate. Molecules that bind gratuitously, i.e., without inducing the effects of Protein E polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product, a reporter gene that is responsive to changes in Protein E polynucleotide or polypeptide activity, and binding assays known in the art.

Another example of an assay for Protein E agonists is a competitive assay that combines Protein E and a potential agonist with Protein E binding molecules, recombinant Protein E binding molecules, natural substrates or ligands, or substrate or ligand mimetics, under appropriate conditions for a competitive inhibition assay. Protein E can be labeled, such as by radioactivity or a colorimetric compound, such that the number of Protein E molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing Protein E induced activities, thereby preventing the action or expression of Protein E polypeptides and/or polynucleotides by excluding Protein E polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, J. Neurochem. 56: 560 (1991); *OLIGODEOXY-NUCLEOTIDES AS ANTISENSE INHIBITORS OF GENE EXPRESSION*, CRC Press, Boca Raton, Fla. (1988), for a description of these molecules). Preferred potential antagonists include compounds related to and variants of Protein E.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial Protein E proteins that mediate tissue damage and/or; to block the normal progression of pathogenesis in infections initiated other than by the implantation of in-dwelling devices or by other surgical techniques.

In accordance with yet another aspect of the invention, there are provided Protein E agonists and antagonists, preferably bacteristatic or bactericidal agonists and antagonists.

The antagonists and agonists of the invention may be employed, for instance, to prevent, inhibit and/or treat diseases.

In a further aspect, the present invention relates to mimotopes of the polypeptide of the invention. A mimotope is a peptide sequence, sufficiently similar to the native peptide (sequentially or structurally), which is capable of being recognised by antibodies which recognise the native peptide; or is capable of raising antibodies which recognise the native peptide when coupled to a suitable carrier.

Peptide mimotopes may be designed for a particular purpose by addition, deletion or substitution of elected amino acids. Thus, the peptides may be modified for the purposes of ease of conjugation to a protein carrier. For example, it may be desirable for some chemical conjugation methods to include a terminal cysteine. In addition it may be desirable for peptides conjugated to a protein carrier to include a hydrophobic terminus distal from the conjugated terminus of the peptide, such that the free unconjugated end of the peptide remains associated with the surface of the carrier protein. Thereby presenting the peptide in a conformation which most closely resembles that of the peptide as found in the context of the whole native molecule. For example, the peptides may be altered to have an N-terminal cysteine and a C-terminal hydrophobic amidated tail. Alternatively, the addition or substitution of a D-stereoisomer form of one or more of the amino acids (inverso sequences) may be performed to create a beneficial derivative, for example to enhance stability of the peptide. Mimotopes may also be retro sequences of the natural peptide sequences, in that the sequence orientation is reversed. Mimotopes may also be retro-inverso in character. Retro, inverso and retro-inverso peptides are described in WO 95/24916 and WO 94/05311.

Alternatively, peptide mimotopes may be identified using antibodies which are capable themselves of binding to the polypeptides of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native polypeptide.

Vaccines

Another aspect of the invention relates to a method for inducing an immunological response in an individual, particularly a mammal, preferably humans, which comprises inoculating the individual with Protein E polynucleotide and/or polypeptide, or a fragment or variant thereof, adequate to produce antibody and/or T cell immune response to protect said individual from infection, particularly bacterial infection and most particularly non typeable *H. influenzae* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of Protein E polynucleotides and/or polypeptides, or a fragment or a variant thereof, for expressing Protein E polynucleotides and/or polypeptides, or a fragment or a variant thereof in vivo in order to induce an immunological response, such as, to produce antibody and/or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when introduced into an individual, preferably a human, capable of having induced within it an immunological response, induces an immunological response in such individual to a Protein E polynucleotide and/or polypeptide encoded therefrom, wherein the composition comprises a recombinant Protein E polynucleotide and/or polypeptide encoded therefrom and/or comprises DNA and/or RNA which encodes and expresses an antigen of said Protein E polynucleotide, polypeptide encoded therefrom, or other polypeptide of the invention. The immunological response may be used therapeutically or prophylactically and may take the form of antibody immunity and/or cellular immunity, such as cellular immunity arising from CTL or CD4+ T cells.

Protein E polypeptides or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein or protein D from *Haemophilus influenzae* (EP 594610), Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein.

In a vaccine composition according to the invention, a Protein E polypeptides and/or polynucleotides, or a fragment, or a mimotope, or a variant thereof may be present in a vector, such as the live recombinant vectors described above for example live bacterial vectors.

Also suitable are non-live vectors for the Protein E polypeptides, for example bacterial outer-membrane vesicles or "blebs". OM blebs are derived from the outer membrane of the two-layer membrane of Gram-negative bacteria and have been documented in many Gram-negative bacteria (Zhou, L et al. 1998. *FEMS Microbiol. Lett.* 163:223-228) including *C. trachomatis* and *C. psittaci*. A non-exhaustive list of bacterial pathogens reported to produce blebs also includes: *Bordetella pertussis, Borrelia burgdorferi, Brucella melitensis, Brucella ovis, Escherichia coli, Haemophilus influenzae, Legionella pneumophila, Moraxella catarrhalis, Neisseria gonorrhoeae, Neisseria meningitidis, Pseudomonas aeruginosa* and *Yersinia enterocolitica*.

Blebs have the advantage of providing outer-membrane proteins in their native conformation and are thus particularly useful for vaccines. Blebs can also be improved for vaccine use by engineering the bacterium so as to modify the expression of one or more molecules at the outer membrane. Thus for example the expression of a desired immunogenic protein at the outer membrane, such as the Protein E polypeptides, can be introduced or upregulated (e.g. by altering the promoter). Instead or in addition, the expression of outer-membrane molecules which are either not relevant (e.g. unprotective antigens or immunodominant but variable proteins) or detrimental (e.g. toxic molecules such as LPS, or potential inducers of an autoimmune response) can be downregulated. These approaches are discussed in more detail below.

The non-coding flanking regions of the Protein E genes contain regulatory elements important in the expression of the gene. This regulation takes place both at the transcriptional and translational level. The sequence of these regions, either upstream or downstream of the open reading frame of the gene, can be obtained by DNA sequencing. This sequence information allows the determination of potential regulatory motifs such as the different promoter elements, terminator sequences, inducible sequence elements, repressors, elements responsible for phase variation, the shine-dalgarno sequence, regions with potential secondary structure involved in regulation, as well as other types of regulatory motifs or sequences. This sequence is a further aspect of the invention.

This sequence information allows the modulation of the natural expression of the Protein E genes. The upregulation of the gene expression may be accomplished by altering the promoter, the shine-dalgarno sequence, potential repressor or operator elements, or any other elements involved. Likewise, downregulation of expression can be achieved by similar types of modification. Alternatively, by changing phase variation sequences, the expression of the gene can be put under phase variation control, or it may be uncoupled from this regulation. In another approach, the expression of the gene can be put under the control of one or more inducible elements allowing regulated expression. Examples of such regulation include, but are not limited to, induction by temperature shift, addition of inductor substrates like selected carbohydrates or their derivatives, trace elements, vitamins, co-factors, metal ions, etc.

Such modifications as described above can be introduced by several different means. The modification of sequences involved in gene expression can be carried out in vivo by random mutagenesis followed by selection for the desired phenotype. Another approach consists in isolating the region of interest and modifying it by random mutagenesis, or site-directed replacement, insertion or deletion mutagenesis. The modified region can then be reintroduced into the bacterial genome by homologous recombination, and the effect on gene expression can be assessed. In another approach, the sequence knowledge of the region of interest can be used to replace or delete all or part of the natural regulatory sequences. In this case, the regulatory region targeted is isolated and modified so as to contain the regulatory elements from another gene, a combination of regulatory elements from different genes, a synthetic regulatory region, or any other regulatory region, or to delete selected parts of the wild-type regulatory sequences. These modified sequences can then be reintroduced into the bacterium via homologous recombination into the genome. A non-exhaustive list of preferred promoters that could be used for up-regulation of gene expression includes the promoters porA, porB, lbpB, tbpB, p110, lst, hpuAB from *N. meningitidis* or *N. gonorroheae*; ompCD, copB, lbpB, ompE, UspA1; UspA2; TbpB from *M. Catarrhalis*; p1, p2, p4, p5, p6, lpD, tbpB, D15, Hia, Hmw1, Hmw2 from *H. influenzae*.

In one example, the expression of the gene can be modulated by exchanging its promoter with a stronger promoter (through isolating the upstream sequence of the gene, in vitro modification of this sequence, and reintroduction into the genome by homologous recombination). Upregulated expression can be obtained in both the bacterium as well as in the outer membrane vesicles shed (or made) from the bacterium.

In other examples, the described approaches can be used to generate recombinant bacterial strains with improved characteristics for vaccine applications. These can be, but are not limited to, attenuated strains, strains with increased expression of selected antigens, strains with knock-outs (or decreased expression) of genes interfering with the immune response, strains with modulated expression of immunodominant proteins, strains with modulated shedding of outer-membrane vesicles.

Thus, also provided by the invention is a modified upstream region of the Protein E genes, which modified upstream region contains a heterologous regulatory element which alters the expression level of the Protein E proteins located at the outer membrane. The upstream region according to this aspect of the invention includes the sequence upstream of the Protein E genes. The upstream region starts immediately upstream of the Protein E genes and continues usually to a position no more than about 1000 bp upstream of the gene from the ATG start codon. In the case of a gene located in a polycistronic sequence (operon) the upstream region can start immediately preceding the gene of interest, or preceding the first gene in the operon. Preferably, a modified upstream region according to this aspect of the invention contains a heterologous promotor at a position between 500 and 700 bp upstream of the ATG.

The use of the disclosed upstream regions to upregulate the expression of the Protein E genes, a process for achieving this through homologous recombination (for instance as described in WO 01/09350 incorporated by reference herein), a vector comprising upstream sequence suitable for this purpose, and a host cell so altered are all further aspects of this invention.

Thus, the invention provides a Protein E polypeptides, in a modified bacterial bleb. The invention further provides modified host cells capable of producing the non-live membrane-based bleb vectors. The invention further provides nucleic acid vectors comprising the Protein E genes having a modified upstream region containing a heterologous regulatory element.

Further provided by the invention are processes to prepare the host cells and bacterial blebs according to the invention.

Also provided by this invention are compositions, particularly vaccine compositions, and methods comprising the polypeptides and/or polynucleotides of the invention and immunostimulatory DNA sequences, such as those described in Sato, Y. et al. Science 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in animal models of infection with non typeable *H. influenzae*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly non typeable *H. influenzae* infection, in mammals, particularly humans.

The invention also includes a vaccine formulation which comprises an immunogenic recombinant polypeptide and/or polynucleotide of the invention together with a suitable carrier, such as a pharmaceutically acceptable carrier. Since the polypeptides and polynucleotides may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

The vaccine formulation of the invention may also include adjuvant systems for enhancing the immunogenicity of the formulation. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4+ve T cell clones by Mosmann and Coffman (Mosmann, T. R. and Coffman, R. L. (1989) *TH1 and TH2 cells: different patterns of lymphokine secretion lead to different functional properties. Annual Review of Immunology,* 7, p 145-173). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast, TH2-type responses are associated with the secretion of IL-4, IL-5, IL-6 and IL-13.

It is known that certain vaccine adjuvants are particularly suited to the stimulation of either TH1 or TH2-type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+ cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (European Patent number 0 689 454).

3D-MPL will be present in the range of 10 μg-100 μg preferably 25-50 μg per dose wherein the antigen will typically be present in a range 2-50 μg per dose.

Another preferred adjuvant comprises QS21, an Hplc purified non-toxic fraction derived from the bark of *Quillaja Saponaria Molina*. Optionally this may be admixed with 3 De-O-acylated monophosphoryl lipid A (3D-MPL), optionally together with an carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 10:1; preferably 1:5 to 5:1 and often substantially 1:1. The preferred range for optimal synergy is 2.5:1 to 1:1 3D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 μg-200 μg, such as 10-100 μg, preferably 10 μg-50 μg per dose. Typically the oil in water will comprise from 2 to 10% squalene, from 2 to 10% alpha tocopherol and from 0.3 to 3% tween 80. Preferably the ratio of squalene:alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

While the invention has been described with reference to certain Protein E polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides. Preferred fragments/peptides are described in Example 10.

The present invention also provides a polyvalent vaccine composition comprising a vaccine formulation of the invention in combination with other antigens, in particular antigens useful for treating otitis media. Such a polyvalent vaccine composition may include a TH-1 inducing adjuvant as hereinbefore described.

In a preferred embodiment, the polypeptides, fragments and immunogens of the invention are formulated with one or more of the following groups of antigens: a) one or more pneumococcal capsular polysaccharides (either plain or conjugated to a carrier protein); b) one or more antigens that can protect a host against *M. catarrhalis* infection; c) one or more protein antigens that can protect a host against *Streptococcus pneumoniae* infection; d) one or more further non typeable *Haemophilus influenzae* protein antigens; e) one or more antigens that can protect a host against RSV; and f) one or more antigens that can protect a host against influenza virus. Combinations with: groups a) and b); b) and c); b), d), and a) and/or c); b), d), e), f), and a) and/or c) are preferred. Such vaccines may be advantageously used as global otitis media vaccines.

The pneumococcal capsular polysaccharide antigens are preferably selected from serotypes 1, 2, 3, 4, 5, 6B, 7F, 8, 9N, 9V, 10A, 11A, 12F, 14, 15B, 17F, 18C, 19A, 19F, 20, 22F, 23F and 33F (most preferably from serotypes 1, 3, 4, 5, 6B, 7F, 9V, 14, 18C, 19F and 23F).

Preferred pneumococcal protein antigens are those pneumococcal proteins which are exposed on the outer surface of the pneumococcus (capable of being recognised by a host's immune system during at least part of the life cycle of the pneumococcus), or are proteins which are secreted or released by the pneumococcus. Most preferably, the protein is a toxin, adhesin, 2-component signal tranducer, or lipoprotein of *Streptococcus pneumoniae*, or fragments thereof. Particularly preferred proteins include, but are not limited to: pneumolysin (preferably detoxified by chemical treatment or mutation) [Mitchell et al. Nucleic Acids Res. 1990 Jul. 11; 18(13): 4010 "Comparison of pneumolysin genes and proteins from *Streptococcus pneumoniae* types 1 and 2.", Mitchell et al. Biochim Biophys Acta 1989 Jan. 23; 1007(1): 67-72 "Expression of the pneumolysin gene in *Escherichia coli*: rapid purification and biological properties.", WO 96/05859 (A. Cyanamid), WO 90/06951 (Paton et al), WO 99/03884 (NAVA)]; PspA and transmembrane deletion variants thereof (WO 92/14488; WO 99/53940; U.S. Pat. No. 5,804,193—Briles et al.); PspC and transmembrane deletion variants thereof (WO 99/53940; WO 97/09994—Briles et al); PsaA and transmembrane deletion variants thereof (Berry & Paton, Infect Immun 1996 December; 64(12):5255-62 "Sequence heterogeneity of PsaA, a 37-kilodalton putative adhesin essential for virulence of *Streptococcus pneumoniae*"); pneumococcal choline binding proteins and transmembrane deletion variants thereof; CbpA and transmembrane deletion variants thereof (WO 97/41151; WO 99/51266); Glyceraldehyde-3-phosphate—dehydrogenase (Infect. Immun. 1996 64:3544); HSP70 (WO 96/40928); PcpA (Sanchez-Beato et al. *FEMS Microbiol Lett* 1998, 164:207-14); M like protein, SB patent application No. EP 0837130; and adhesin 18627 (SB Patent application No. EP 0834568). Further preferred pneumococcal protein antigens are those disclosed in WO 98/18931, particularly those selected in WO 98/18930 and PCT/US99/30390.

Preferred *Moraxella catarrhalis* protein antigens which can be included in a combination vaccine (especially for the prevention of otitis media) are: OMP106 [WO 97/41731 (Antex) & WO 96/34960 (PMC)]; OMP21; LbpA &/or LbpB [WO 98/55606 (PMC)]; TbpA &/or TbpB [WO 97/13785 & WO 97/32980 (PMC)]; CopB [Helminen M E, et al. (1993) Infect. Immun. 61:2003-2010]; UspA1 and/or UspA2 [WO 93/03761 (University of Texas)]; OmpCD; HasR (PCT/EP99/03824); PilQ (PCT/EP99/03823); OMP85 (PCT/EP00/01468); lipo06 (GB 9917977.2); lipo10 (GB 9918208.1); lipo11 (GB 9918302.2); lipo18 (GB 9918038.2); P6 (PCT/EP99/03038); D15 (PCT/EP99/03822); OmplA1 (PCT/EP99/06781); Hly3 (PCT/EP99/03257); and OmpE.

Preferred further non-typeable *Haemophilus influenzae* protein antigens which can be included in a combination vaccine (especially for the prevention of otitis media) include: Fimbrin protein [(U.S. Pat. No. 5,766,608—Ohio State Research Foundation)] and fusions comprising peptides therefrom [eg LB1 (f) peptide fusions; U.S. Pat. No. 5,843,464 (OSU) or WO 99/64067]; OMP26 [WO 97/01638 (Cortecs)]; P6 [EP 281673 (State University of New York)]; protein D (EP 594610); TbpA and/or TbpB; Hia; Hsf; Hin47; Hif; Hmw1; Hmw2; Hmw3; Hmw4; Hap; D15 (WO 94/12641); P2; P5 (WO 94/26304); NlpC2 (BASB205) [WO 02/30971]; Slp (BASB203) [WO 02/30960]; and iOMP1681 (BASB210) [WO 02/34772].

Preferred influenza virus antigens include whole, live or inactivated virus, split influenza virus, grown in eggs or MDCK cells, or Vero cells or whole flu virosomes (as described by R. Gluck, Vaccine, 1992, 10, 915-920) or purified or recombinant proteins thereof, such as HA, NP, NA, or M proteins, or combinations thereof.

Preferred RSV (Respiratory Syncytial Virus) antigens include the F glycoprotein, the G glycoprotein, the HN protein, or derivatives thereof.

Compositions, Kits and Administration

In a further aspect of the invention there are provided compositions comprising a Protein E polynucleotides and/or a Protein E polypeptides for administration to a cell or to a multicellular organism.

The invention also relates to compositions comprising a polynucleotide and/or a polypeptides discussed herein or their agonists or antagonists. The polypeptides and polynucleotides of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides, polynucleotides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, solutions, powders and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The dosage range required depends on the choice of peptide, the route of administration, the nature of the formulation, the nature of the subject's condition, and the judgment of the attending practitioner. Suitable dosages, however, are in the range of 0.1-100 µg/kg of subject.

A vaccine composition is conveniently in injectable form. Conventional adjuvants may be employed to enhance the immune response. A suitable unit dose for vaccination is 0.5-5 microgram/kg of antigen, and such dose is preferably administered 1-3 times and with an interval of 1-3 weeks. With the indicated dose range, no adverse toxicological effects will be observed with the compounds of the invention which would preclude their administration to suitable individuals.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Sequence Databases, Sequences in a Tangible Medium, and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as the GCG program package.

Also provided by the invention are methods for the analysis of character sequences or strings, particularly genetic sequences or encoded protein sequences. Preferred methods of sequence analysis include, for example, methods of sequence homology analysis, such as identity and similarity analysis, DNA, RNA and protein structure analysis, sequence assembly, cladistic analysis, sequence motif analysis, open reading frame determination, nucleic acid base calling, codon usage analysis, nucleic acid base trimming, and sequencing chromatogram peak analysis.

A computer based method is provided for performing homology identification. This method comprises the steps of: providing a first polynucleotide sequence comprising the sequence of a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

DEFINITIONS

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biol-* ogy, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heine, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.,* 48: 1073 (1988). Methods to determine identity are designed to give the largest match between the sequences tested. Moreover, methods to determine identity are codified in publicly available computer programs. Computer program methods to determine identity between two sequences include, but are not limited to, the GAP program in the GCG program package (Devereux, J., et al., *Nucleic Acids Research* 12(1): 387 (1984)), BLASTP, BLASTN (Altschul, S. F. et al., *J. Molec. Biol.* 215: 403-410 (1990), and FASTA (Pearson and Lipman Proc. Natl. Acad. Sci. USA 85; 2444-2448 (1988). The BLAST family of programs is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990). The well known Smith Waterman algorithm may also be used to determine identity.

Parameters for polypeptide sequence comparison include the following:
Algorithm: Needleman and Wunsch, J. Mol Biol. 48: 443-453 (1970)
Comparison matrix: BLOSSUM62 from Henikoff and Henikoff, Proc. Natl. Acad. Sci. USA. 89:10915-10919 (1992)
Gap Penalty: 8
Gap Length Penalty: 2
A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:
Algorithm: Needleman and Wunsch, J. Mol Biol. 48: 443-453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO: 11, wherein said polynucleotide sequence may be identical to the reference sequence of SEQ ID NO: 11 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO: 11 by the integer defining the percent identity divided by 100 and then subtracting that product from said total number of nucleotides in SEQ ID NO: 11, or:

$$n_n \leq x_n - (x_n \cdot y),$$

wherein $n_n$ is the number of nucleotide alterations, $x_n$ is the total number of nucleotides in SEQ ID NO: 11, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of polynucleotide sequences encoding the polypeptides of SEQ ID NO:1-10 may create nonsense, missense or frameshift mutations in this coding sequence and thereby alter the polypeptide encoded by the polynucleotide following such alterations.

By way of example, a polynucleotide sequence of the present invention may be identical to the reference sequences of SEQ ID NO: 11, that is it may be 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO: 11 by the integer defining the percent identity divided by 100 and then subtracting that product from said total number of nucleic acids in SEQ ID NO: 11, or:

$$n_n \leq x_n - (x_n \cdot y),$$

wherein $n_n$ is the number of nucleic acid alterations, $x_n$ is the total number of nucleic acids in SEQ ID NO: 11, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to the polypeptide reference sequence of SEQ ID NO:1-10, wherein said polypeptide sequence may be identical to the reference sequence of SEQ ID NO:1-10 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:1-10 by the integer defining the percent identity divided by 100 and then subtracting that product from said total number of amino acids in SEQ ID NO:1-10, respectively, or:

$$n_a \leq x_a - (x_a \cdot y),$$

wherein $n_a$ is the number of amino acid alterations, $x_a$ is the total number of amino acids in SEQ ID NO:1-10, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:1-10, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:1-10 by the integer defining the percent identity divided by 100 and then subtracting that product from said total number of amino acids in SEQ ID NO:1-10, or:

$$n_a \le x_a - (x_a \cdot y),$$

wherein $n_a$ is the number of amino acid alterations, $x_a$ is the total number of amino acids in SEQ ID NO:1-10, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Individual(s)," when used herein with reference to an organism, means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxyribonucleotide, which may be unmodified RNA or DNA or modified RNA or DNA including single and double-stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Disease(s)" means any disease caused by or related to infection by a bacteria, including, for example, otitis media in infants and children, pneumonia in elderlies, sinusitis, nosocomial infections and invasive diseases, chronic otitis media with hearing loss, fluid accumulation in the middle ear, auditive nerve damage, delayed speech learning, infection of the upper respiratory tract and inflammation of the middle ear.

Experimental Part

The examples below are carried out using standard techniques, which are well known and routine to those of skill in the art, except where otherwise described in detail. The examples are illustrative, but do not limit the invention The present investigation describes the isolation, purification, characterization, cloning and expression of the novel outer membrane protein named protein E (pE) of *H. influenzae* and the novel truncated recombinant pE(A), which was discovered using a human IgD(λ) myeloma serum.

Materials and Methods

Reagents

The type b *H. influenzae* strains MinnA and NTHi3655 were kindly obtained from Robert S. Munson Jr. (Washington University School of Medicine (St. Louis, Mo.). The non-typable *H. influenzae* strain NTHi772 was a clinical isolate from a nasopharyngeal swab culture at our Department (2). A series of different *Haemophilus* species was also analysed and is described in Table 1. The human IgD myeloma whole serum IgD(λ) was purchased from The Binding Site (Birmingham, England). To produce a specific anti-pE antiserum, rabbits were immunized intramuscularly with 200 μg of recombinant pE22-160 [pE(A)] emulsified in complete Freunds adjuvant (Difco, Becton Dickinson, Heidelberg, Germany) or pE41-68 peptide conjugated to keyhole limpet hemocyanin (KLH) and boosted on days 18 and 36 with the same dose of protein in incomplete Freunds adjuvans. Blood was drawn 2 to 3 weeks later. Resulting polyclonal antibodies were isolated by affinity chromatography using pE(A) or a specific pE peptide (pE41-68) conjugated to CnBr-Sepharose (11). Horseradish peroxidase (HRP)-conjugated goat anti-human IgD was from Biosource (Camarillo, Calif.). Rabbit anti-human IgD pAb were from Dakopatts (Gentofte, Denmark).

Fluoresceinisothiocyanate (FITC)-conjugated mouse anti-human IgD, HRP-conjugated rabbit anti-human light chains (κ and λ), and FITC-conjugated swine anti-rabbit polyclonal immunoglobulins were purchased from Dakopatts. Extraction and purification of protein E

*H. influenzae* type b (MinnA) was grown overnight in brain heart infusion (BRI) broth (Difco Laboratories, Detroit, Mich.) supplemented with NAD and hemin (Sigma, St. Louis, Mo.), each at 10 μg/ml. After two washes the bacteria were extracted in 0.05 M Tris-HCl-buffer (pH 8.8) containing 0.5% Empigen® (Calbiochem Novabiochem, Bedford, Mass.). The bacterial suspension was mixed by magnetic stirring for 2 h at 37° C. After centrifugation at 8000×g for 20 min at 4° C., the supernatant was filtrated with sterile filter (0.45 μm; Sterivex-HV™, Millipore). *H. influenzae* extract in 0.5% Empigen® was applied to a Q-sepharose column (Amersham Pharmacia Biotech) equilibrated with 0.05 M Tris-HCl (pH 8.8) containing 6 M urea. The column was eluted using a 0 to 1 M NaCl linear gradient in the same buffer. Fractions that were detected by the IgD(A) myeloma serum were pooled, dialyzed in Spectraphor membrane tubes (molecular weight cut off 6-8,000; Spectrum, Laguna hills, CA) against 0.05 M Tris-HCl, pH 8.8, and concentrated on YM100 disc membranes (molecular weight cut off 10,000; Amicon, Beverly, Mass.).

SDS-PAGE and Detection of Proteins on Membranes (Western Blot)

SDS-PAGE was run at 150 constant voltage using 10% Bis-Tris gels with running (MES), sample (LDS), and transfer buffer as well as a blotting instrument from Novex (San Diego, Calif.). Samples were regularly heated at 100° C. for 10 min. Gels were stained with Coomassie Brilliant Blue R-250 (13; Bio-Rad, Sundbyberg, Sweden). Electrophoretical transfer of protein bands from the gel to an immobilon-P membrane (Millipore, Bedford, Mass.) was carried out at 30 V for 2 to 3 h. After transfer, the immobilon-P membrane was blocked in PBS with 0.05% Tween 20 (PBS-Tween) containing 5% milk powder. After several washings in PBS-Tween, the membrane was incubated with purified IgD myeloma protein (0.5 µg/ml, hu IgD(λ) myeloma; The Bindingsite) in PBS-Tween including 2% milk powder for 1 h at room temperature. HRP-conjugated goat anti-human IgD diluted 1/1000 was added after several washings in PBS-Tween. After incubation for 40 min at room temperature and several additional washings in PBS-Tween, development was performed with ECL Western blotting detection reagents (Amersham Pharmacia Biotech, Uppsala, Sweden).

Two-Dimensional SDS-Polyacrylamide Gel Electrophoresis (2-D PAGE) and Western Blot After ion exchange chromatography, Empigen® extracts of *H. influenzae* (MinnA) were subjected to isoelectric focusing (IEF) using the IPGphor IEF System (Amersham Pharmacia Biotech) (5,12). For gel calibration, a standard was used (cat. no. 161-0320; Bio-Rad). 2-D polyacrylamide gels were electroblotted to Immobilon-PVDF filters (0.45 mm; Millipore, Bedford, US) at 120 mA over night. After saturation, incubation, blocking and washing steps were performed as described above.

Amino Acid Sequence Analysis

Automated amino acid sequence analysis was performed with an Applied Biosystems (Foster City, Calif.) 470A gasliquid solid phase sequenator.

Construction of a *H. influenzae* Genomic Library

Chromosomal DNA was prepared from strain 772 by using a modification of the method of Berns and Thomas (2,13). Briefly, an *H. influenzae* 772 genomic library was constructed from 40 µg of DNA which was partially digested with Sau3A for 1 h. The cleaved DNA was fractionated on a sucrose gradient (14). Fractions containing DNA fragments of appropriate sizes (2 to 7 kbp) were pooled, and the DNA was ligated to BamHI-digested pUC18 followed by transformation into *Escherichia coli* JM83 by electroporation using a Gene pulser (Bio-Rad, Richmond Calif.). The bacteria was plated onto LB agar supplemented with ampicillin and X-Gal (5-bromo-4-chloro-3-indolyl-β-D-galac-topyranoside).

Colony Immunoassay, DNA Isolation and Sequencing

The *E. coli* transformants, cultivated overnight on LB agar, were transferred to nitrocellulose filters (Sartorius, Gottingen, Germany) by covering the agar surfaces with dry filters. The plates were left for 15 min, and the cells were lysed by exposure to saturated chloroform vapor for 20 min. Residual protein-binding sites on the filters were blocked by incubating the filters in Tris balanced saline containing ovalbumin (50 mM Tris-hydrochloride, 154 roM NaCl, 1.5% ovalbumin [pH 7.4 J) for 30 min. After being blocked, the filters were incubated with human IgD(A) for 30 min. HRP-conjugated anti-human IgD polyclonal antibodies were added after washes and the filters were incubated for 30 min. All incubations were done at room temperature. Finally, filters were developed using 4-chloro-1-naphtol and H202. Positive clones were picked and pUC18 plasmid DNA containing NTHi772 genomic DNA was purified. The resulting NTHi772 DNA insert was sequenced using the flanking primers M13+ and M13− and the Bigdye® Terminator Cycle Sequencing v. 2.0 Ready reaction sequencing kit (PerkinElmer, Foster City, Ca). The obtained insert sequence (3.55 kbp) corresponded to a stretch containing DNA encoding the proteins HI0175, HI0176, HI0177, and finally HI0178 (15).

DNA Cloning and Protein Expression

Figure 8:
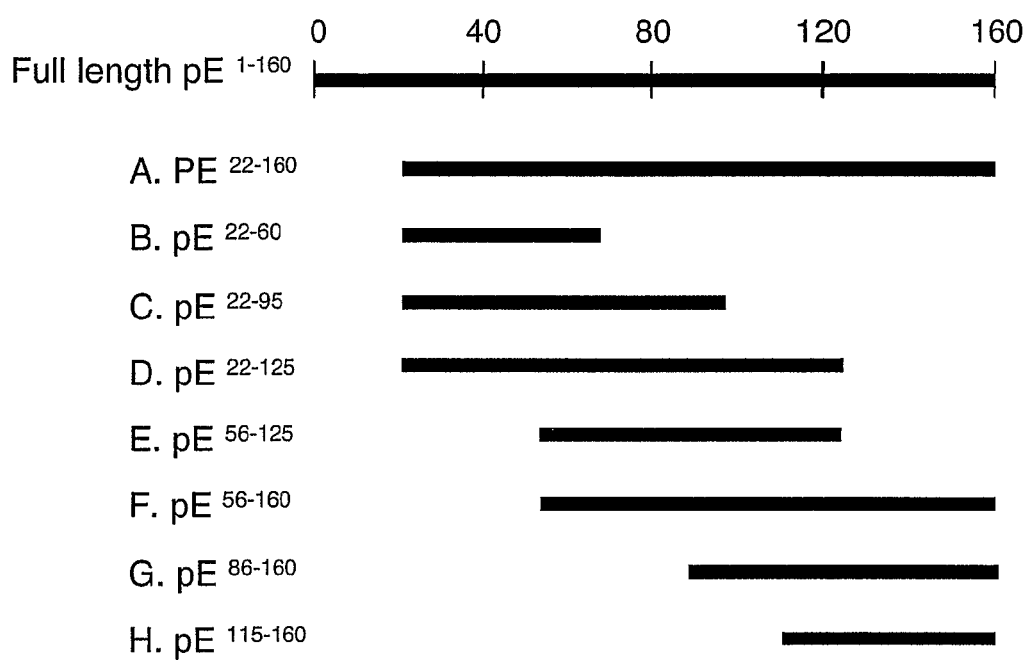
FIG. 8. SDS-PAGE demonstrating recombinant pE22-160 (fragment A) and a series of truncated fragments designated B to H. In A, an outline of the different fragments are shown, whereas in B, an SDS-PAGE is demonstrated. DNA encoding the various proteins were ligated into the expression vector pET26(+) and recombinantly expressed in *E. coli*. Resulting overexpressed proteins were purified on nickel resins and subjected to separation on a SDS-PAGE followed by Coomassie brilliant blue staining.
Figure 8:
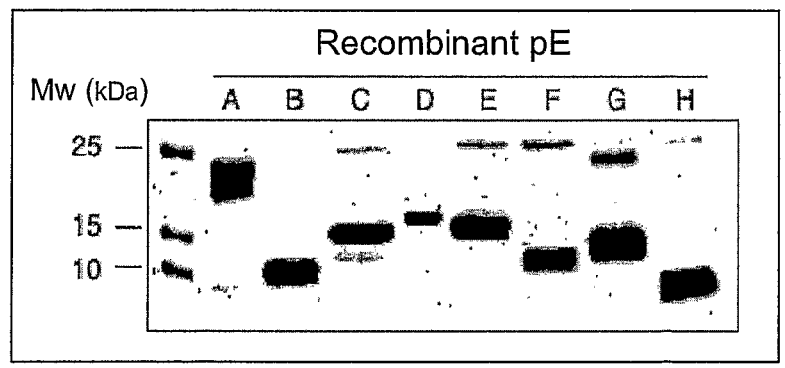

All constructs were manufactured using PCR amplified fragments. pUC18 containing NTHi 772 genomic DNA (HI0175 to HI0178) was used as template. Taq DNA polymerase was from Roche (Mannheim, Germany) and PCR conditions were as recommended by the manufacturer. The open reading frames of the four predictive proteins HI0175 to HI0178 were cloned, but only the procedure describing cloning of HID (HI0178) has been included here. $pE^{22-160}$ [designated pE(A)] was devoid of the endogenous signal peptide including amino acid residue glutamine[21] and was amplified by PCR using primers 5"_ctcaggatccaaaggctgaacaaaatgatgtg-3' (SEQ ID NO: 13) and 5"_ggtgcagattaagctttttttat-caactg-3' (SEQ ID NO: 14) introducing the restriction enzyme sites BamHI and HindIII. To fuse 6 histidine residues (SEQ ID NO: 12) encoded by the expression vector, the $pE^{22-160}$ stop codon was mutated. The resulting 417 bp open reading frame of the pe gene was ligated into pET26(+) (Novagen, Darmstadt, Germany). To avoid presumptive toxicity, the resulting plasmids were first transformed into the host *E. coli* DH5. Thereafter, the plasmids encoding pE and pE(A) were transformed into the expressing host BL21 (DE3). In addition to full length pE and pE(A), a series of truncated pE variants were manufactured. An outline is shown in FIG. 8. Primers containing BamHI and HindIII were used for all constructs. The procedures for the truncated variants were as described above. All constructs were sequenced using the Bigdye® Terminator Cycle Sequencing v. 2.0 Ready reaction sequencing kit (Perkin-Elmer, Foster City, Ca).

To produce recombinant proteins, bacteria were grown to mid-log phase ($OD_{600}$ 0.6 to 0.8) followed by induction with 1 mM isopropyl-1-thio-β-D-galactoside (IPTG) resulting in overexpression of pE(A). When $OD_{600}$ reached 1.5 to 1.7, bacteria were harvested and inclusion bodies isolated according to a standard protocol. Recombinant proteins could be further purified by affinity chromatography using nickel columns. Purified recombinant proteins were subsequently analysed by SDS-PAGE.

*H. influenzae* DNA Purification, PCR Conditions and Sequencing

Genomic DNA from *H. influenzae* clinical isolates was isolated using a DNeasy™ Tissue kit (Qiagen, Hilden, Ger. Taq DNA polymerase was from Roche (Mannheim, Ger and PCR conditions were as recommended by the manufacturer. To isolate the pe gene, the primer pair 5'-gcatttattaggtcagtt-tattg-3' (SEQ ID NO: 15) and 5'-gaaggattatttctgatgcag-3' (SEQ ID NO: 16), which anneal to the flanking genes HI0177 respectively HI0179, were used. Resulting PCR products (948 bp) were sequenced by gene-walking using the above mentioned primers in addition to the primers 5'-cttgggttacttaccgcttg-3' (SEQ ID NO: 17) and 5'-gtgttaaacttaacgtatg-3' (SEQ ID NO: 18). Capillary electrophoresis was run on a Beckman CEQ 2000 using a dye-terminator cycle sequencing kit (CEQ DTCS kit, Beckman Coulter, Stockholm, Sweden). Editing and alignment of the resulting DNA sequences were performed using PHRED (CodonCode, Deadham, USA) and SEQUENCHER (MedProbe, Oslo, Norway).

Manufacture of a pE-Deficient *H. influenzae* (NTHi 3655 Δpe)

Genomic DNA isolated from NTHi 772 was used as template. The 5'- and 3'-ends of pe including parts of the genes HI0177 and HI0179 were amplified as two cassettes (815 bp and 836 bp, respectively) using DyNAzyme™ II DNA polymerase (Finnzymes, Espoo, Finland) introducing the restriction enzyme sites XhoI and EcoRI respectively EcoRI and SpEI in addition to specific uptake sequences in the two cassettes (18). Resulting PCR fragments were digested and cloned into pBluescript SK (+/−). A kanamycin resistance gene cassette (1282 bp) was obtained from pUC4K using the restriction enzyme site for EcoRI. After digestion, the PCR product was ligated into the truncated pe gene fragment containing parts of the HI0177 and HI0179 genes. *H. influenzae* strains Eagan and RM804 were transformed according to the M-IV method of Heriott et al. (19). Resulting mutants were verified by PCR and the pE expression was analysed by Western blot and flow cytometry.

Molecular Biology Softwares

Obtained sequences were compared with the available *H. influenzae* KW20 genome (http://www.tigr.org) (15). The signal peptide was deduced using the SignalP V1.1 World Wide Web Prediction Server Center for Biological Sequence Analysis (http://www.cbs.dtu.dk/services/SignalP/) (16). The pE hydrophobicity profile was analysed by the method of Kyte and Doolittle (17).

Animals, Surgical Procedures and Rat Otitis Media Model

Healthy male Sprague-Dawley rats, weighing 200-250 g were used. All animals were free of middle ear infections as determined by otomicroscopy before operation. At interventions, rats were anesthezised with methohexital (Brietal®, Elli Lilly and Company, Indianapolis, Ind.) intravenously or chloral hydrate (apoteksbolaget, Lund, Sweden) intraperitoneally. Bacteria for animal experiments were grown as described above. After harvesting by centrifugation, the baceria were resuspended in fresh culture media to a concentration of $2\times10^{10}$ colony forming units (cfu) for both NTHi 3655 and the corresponding pE mutant. Preparations were kept on ice until use. To induce acute otitis media (AOM), the middle ear was reached by a ventral midline incision in the neck, and approximately 0.05 ml of the bacterial suspension was instilled into the middle ear cavity. Otomicroscopy was performed on days 3 and 5 post-operatively. Otitis media with purulent effusion, i.e., an opaque effusion and often pronounced dilatation of vessels on day 3, was referred to as AOM.

Results

Extraction and Separation of a *H. influenzae* Protein (pE) that is Detected by an IgD(λ) Myeloma Serum It had previously been thought that non-typable *H. influenzae* (NTHi) do not bind IgD (19), whereas encapsulated *H. influenzae* strongly bind IgD. We discovered that an IgD(λ) myeloma serum specifically bound also to NTHi. A typical flow cytometry profile of the NTHi772 is shown in FIG. 1. A strong shift and increased fluorescence was found in the presence of the IgD(λ) myeloma protein as compared to the control without IgD.

To in detail analyse the *H. influenzae* outer membrane protein that was detected by the IgD(λ) myeloma, an outer membrane fraction was solubilized in the detergent Empigen®. FIG. 1B demonstrates that a very strong IgD-binding activity was obtained on Western blots for a protein with an apparent molecular weight of approximately 16 kDa. However, no distinct protein band corresponding to the IgD-binding activity could be detected on the Coomassie Brilliant blue-stained SDS-PAGE. After separation on a Q-Sepharose column, the same outer membrane extract was applied to 2-dimensional gel electrophoresis and silver staining (FIG. 1C). In parallel, a corresponding Western blot probed with human IgD(λ) was performed. The area where pE was localized could thus be encircled. However, no visible protein was observed (FIG. 1C).

Figure 2:
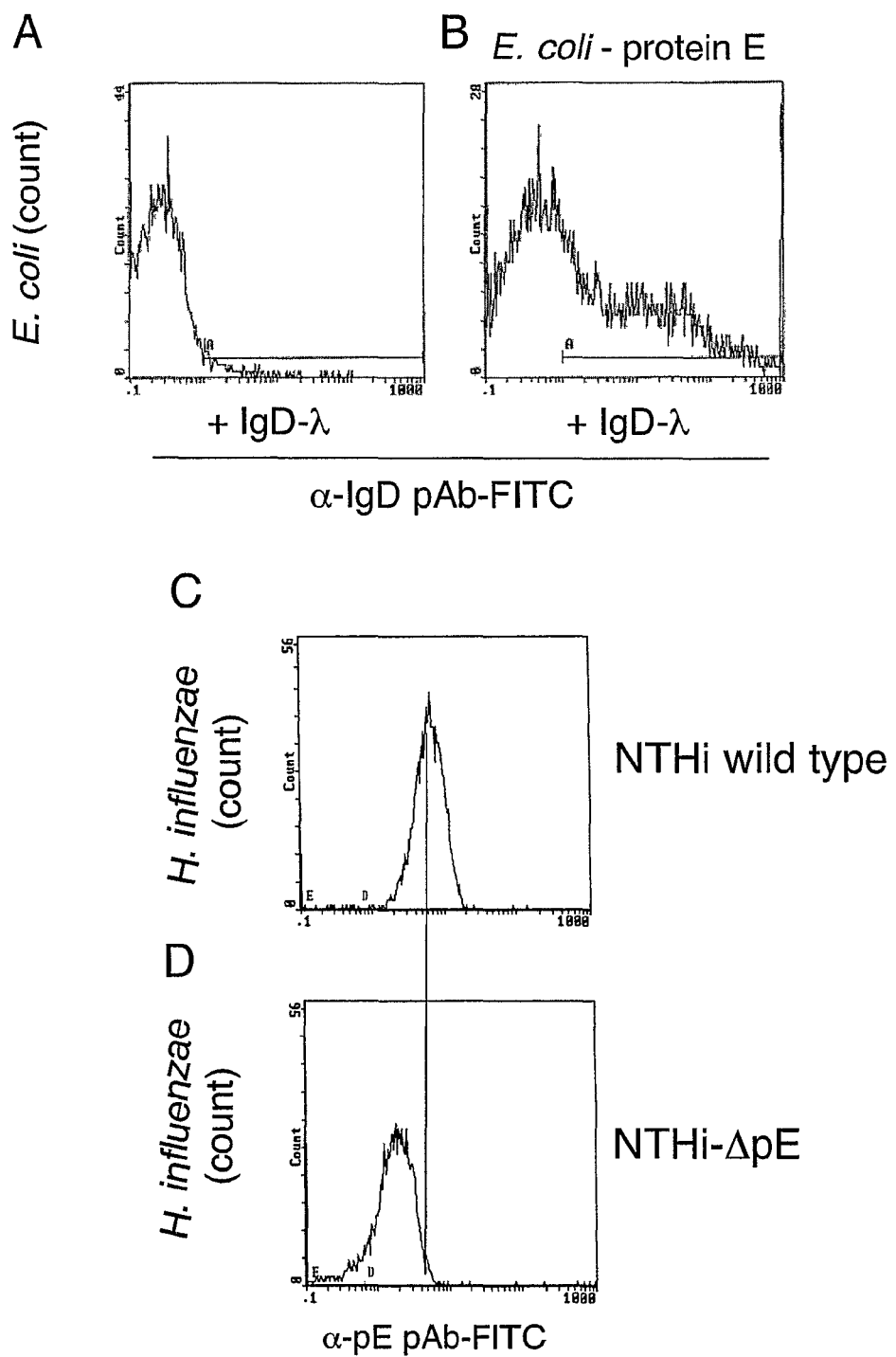
FIG. 2. Flow cytometry profiles of pE-expressing *E. coli* compared to the *H. influenzae* 3655 wild type and a pE deficient mutant. *E. coli* harbouring an empty pUC18 vector (A) is compared to bacteria transformed with pUC18 containing genomic DNA from *H. influenzae* 772 (genes HI0175 to HI0178) (B). pE expression in the non-typable *H. influenzae* 3655 wild type (C) and the corresponding mutant (D) is shown. *E. coli* strain JM83 and *H. influenzae* were grown in liquid cultures overnight. *E. coli* was incubated with human myeloma IgD(λ) on ice. After 1 h and washings, FITC-conjugated rabbit anti-human IgD pAb was added for an additional 30 min followed by washing steps and subsequent flow cytometry analysis. The same procedure was done with *H. influenzae* 3655 or the derived pE mutant using specific rabbit anti-pE polyclonal antibodies and FITC-conjugated goat anti-rabbit pAb.

Cloning of Protein E and Manufacture of a Non-Typable *H. influenzae* Mutant Devoid of pE Since we could not detect any protein in the 2-D analysis after separation, an *H. influenzae* DNA library was constructed using the non-typable *H. influenzae* (NTHi) strain 772. Genomic DNA containing fragments in the range of 2 to 7 kbp was ligated into pUC18 followed by transformation into *E. coli* JM83. Transformants were analysed for IgD-binding using a colony immunoassay consisting of human IgD(λ) and HRP-conjugated anti-human IgD polyclonal antibodies. Three positive colonies were found out of 20,000 colonies tested and were subjected to a second round of screening with IgD(λ). We sequenced one of the positive clones and found a 3.55 kb insert containing DNA encoding for the four proteins HI0175 to HI0178 according to the physical map of *H. influenzae* KW20 (15). To further verify the specific interaction with IgD(λ), the selected transformant was also analysed by flow cytometry. As can be seen in FIG. 2B, *E. coli* JM83 harbouring *H. influenzae* 772 genomic DNA corresponding to the sequence encoding for HI0175 to HI0178 was detected by IgD(λ) as compared to the negative control *E. coli* transformed with an empty vector only (FIG. 2A).

In addition to analysis of the *E. coli* JM83 clone, the four *H. influenzae* proteins (HI0175 to HI0178) were cloned into the expression vector pET26(+) and produced in *E. coli* BL21DE3. The resulting recombinant proteins were analysed by IgD(λ) on Western blots and HI0178 was found to be the only protein that was detected by IgD(λ) (data not shown).

A non-typable *H. influenzae* (NTHi 3655) was mutated by introduction of a kanamycin resistance gene cassette in the gene encoding for pE. Resulting mutants were confirmed by PCR and the absence of pE expression was proven by analysis of outer membrane proteins in Western blots using a specific anti-pE antiserum (data not shown). The NTHi 3655Δpe mutant was also tested by flow cytometry and a clearly decreased fluorescence was found with the mutant as compared to the corresponding NTHi 3655 wild type when analysed with a rabbit anti-pE monovalent antiserum and a FITC-conjugated goat anti-rabbit secondary pAb (FIGS. 2C and D).

Figure 3:
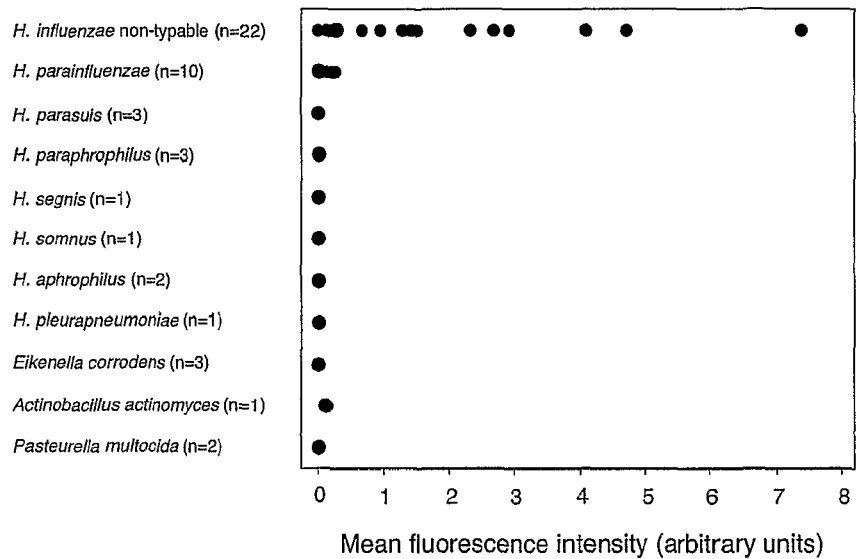
FIG. 3. pE expression of *H. influenzae* and related species as revealed by flow cytometry and an IgD(λ) myeloma serum. Twenty-two strains of NTHi and 27 strains of *haemophilus* species or related bacteria were analysed. Bacteria were grown to stationary phase and incubated with a human myeloma IgD(λ) on ice. After 1 h and washings, FITC-conjugated rabbit anti-human IgD polyclonal antibodies (pAb) were added for an additional 30 min followed by washing steps and subsequent flow cytometry analyses.

Protein E was Detected in all *H. influenzae*, Whereas Other Subspecies were Negative To analyse pE expression of clinical isolates and type strains of NTHi, we developed a direct binding flow cytometry assay consisting of the IgD(λ) serum and a FITC-conjugated secondary antibody directed against human IgD. In initial experiments, bacteria collected at different time points were analysed for pE expression. No difference was observed regarding pE expression between logarithmic growing or stationary phase bacteria, suggesting that NTHi surface pE was not depending on the growth phase. Stationary phase bacteria were thus used in all further analyses. Mean fluorescence intensity (mfi) per bacterial cell was analysed and a total of 22 NTHi strains were included in our study. The fluorescence intensity varied between different NTHi strains, albeit pE was detected in the majority of NTHi in this particular assay using the IgD(λ) myeloma serum as detection antibody (FIG. 3).

In other experiments specific rabbit anti-pE antibodies were used for detection of surface exposed pE. The specific anti-pE antiserum specifically recognized pE also in encapsulated strains of *H. influenzae, H. aegypticus*, and *H. haemolyticus*. (data not shown).

Figure 4:
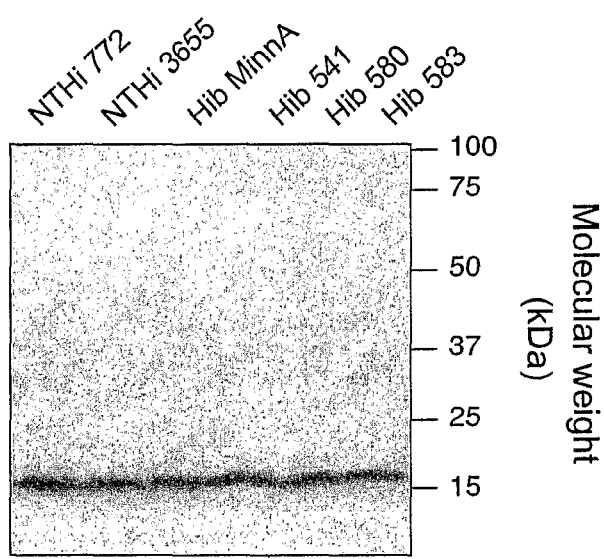
FIG. 4. pE is expressed in NTHi and encapsulated *H. influenzae* as revealed by Western blots. Bacterial proteins from the indicated strains were prepared using Empigen® and subjected to a SDS-gel followed by Western blot probed with human myeloma IgD(λ) and horseradish peroxidase-conjugated goat anti-human IgD polyclonal pAb as detection antibodies.

To further analyse pE expression levels, Empigen® treated outer membrane extracts of various *haemophilus* species were tested in Western blots using IgD(λ) as detection antibody (Table 1). In these experiments, no differences between high and low expressing *haemophilus* strains were found, i.e., in Western blots all strains displayed pE of the same intensity and in the same position corresponding to 16 kDa. Encapsulated *H. influenzae* (type a to f) also expressed pE as revealed by Western blots (Table 1). For example, the pE expression in four *H. influenzae* capsule type b (Hib) is compared to NTHi in FIG. 4. *H. aegypticus*, and *H. haemolyticus* expressed pE (Table 1), whereas for other related *haemophilus* species, that were negative in flow cytometry (FIG. 3), no pE was detected in Western blot analyses. The specific anti-pE antiserum specifically recognized pE also in encapsulated strains (data not shown).

TABLE 1

|     | Encapsulated or non-typable (NT) | Western Blot (positive/negative; 0) |
| --- | --- | --- |
| 556 | *H. influenzae* CCUG EF 6881 I Caps.type a | pos |
| 557 | *H. influenzae* CCUG EF 7315 I Caps.type a | pos |
| 94  | H.i. typ a | pos |
| 479 | *H. influenzae* Minn A type b | pos |
| 547 | *H. influenzae* Eagan type b | pos |
| 485 | *H. influenzae* 85 05 30 b | pos |
| 539 | *H. influenzae* D-22 Caps.type b | pos |
| 541 | *H. influenzae* HK 695 Caps.type b | pos |
| 542 | *H. influenzae* HK 691 Caps.type b | pos |
| 577 | *H. influenzae* HK 713 Caps.type b | pos |
| 578 | *H. influenzae* HK 714 Caps.type b | pos |
| 582 | *H. influenzae* HK 83458 caps type b | pos |
| 581 | *H. influenzae* HK 163 caps type b | pos |
| 580 | *H. influenzae* HK 729 caps type b | pos |
| 569 | *H. influenzae* 17 B Dallas caps type b | pos |
| 568 | *H. influenzae* DL 42/2F4 caps type b | pos |
| 579 | *H. influenzae* HK 720 caps type b | pos |
| 477 | *H. influenzae* 6-460 caps type b | pos |
| 570 | *H. influenzae* DL 42 caps type b | pos |
|     | *H. influenzae* RM 804 no caps type b | pos |
| 583 | *H. influenzae* HK 705 no caps type b | pos |
| 551 | *H. influenzae* CCUG EF 4851 II Caps.type c | pos |
| 552 | *H. influenzae* CCUG EF 4852 II Caps.type c | pos |
| 95  | H.i. typ c | pos |
| 555 | *H. influenzae* CCUG EF 6878 IV Caps.type d | pos |
| 560 | *H. influenzae* CCUG EF NCTC 8470 Caps.type d | pos |
| 96  | H.i. typ d | pos |
| 554 | *H. influenzae* CCUG EF 6877 IV Caps.type e | pos |
| 88  | H.i. typ e A11/01 | pos |
| 89  | H.i. typ e A76/01 | pos |
| 90  | H.i. typ e A77/99 | pos |
| 559 | *H. influenzae* CCUG EF 15519 II Caps.type f | pos |
| 78  | H.i. CCUG 15435 Caps.type f | pos |
| 91  | H.i. typ f A1/01 | pos |
| 92  | H.i. typ f A58/01 | pos |
| 93  | H.i. typ f A91/01 | pos |
| 67  | H.i. NT 6-9547 b.typ I | pos |
| 478 | *H. influenzae* 6-601 NT | pos |
| 484 | *H. influenzae* 6-6200 NT NT | pos |
| 507 | *H. influenzae* 6-102 NT NT | pos |
| 65  | H.i.NT 7-68/99 Claren. lavage | pos |
| 68  | H.i. NT 7-758 | pos |
| 546 | *H. influenzae* 6-9547 NT | pos |
| 480 | *H. influenzae* 772 NT | pos |
| 476 | *H. influenzae* 6-115 NT | pos |
| 481 | *H. influenzae* 6-504 NT | pos |
| 482 | *H. influenzae* 6-7702 NT | pos |
| 483 | *H. influenzae* 82 10 23 NT | pos |
| 486 | *H. influenzae* 6-121 NT | pos |
| 506 | *H. influenzae* 6-6267 NT | pos |
| 540 | *H. influenzae* D-26 NT | pos |
| 543 | *H. influenzae* Buffalo 1479 NT | pos |
| 544 | *H. influenzae* Buffalo C 7961 NT | pos |
| 64  | H.i. 56-2934 000428 NT | pos |
| 69  | H.i. 7-120/99 bronch NT | pos |
| 70  | H.i. 7-161/99 bronch NT | pos |
| 66  | H.i. S6-2952 000428 NT | pos |
| 105 | H.i. RM 3655 NT | pos |
| 531 | *H. aegypticus* EF 628 NT,no b | pos |
| 73  | *H.aegypticus* CCUG 25716 | pos |
| 74  | *H.aegypticus* CCUG 26840 | pos |

TABLE 1-continued

| | Encapsulated or non-typable (NT) | Western Blot (positive/negative; 0) |
|---|---|---|
| 76 | H.aegypticus CCUG 39154 | pos |
| 79 | H.aegypticus HK 1247 | pos |
| 80 | H.aegypticus HK 1229 | pos |
| 81 | H.aegypticus HK 1242 | pos |
| 82 | H.i. biovar aegypticus HK 865 | pos |
| 83 | H.i. biovar aegypticus HK 871 | pos |
| 84 | H.i. biovar aegypticus HK 1222 | pos |
| 85 | H.i. biovar aegypticus HK 1239 | pos |
| 86 | BPF-like disease HK 1212 | pos |
| 87 | BPF-like disease HK 1213 | pos |
| 72 | H.haemolyticus CCUG 15642 | pos |
| 101 | H.haemolyticus 34669/83 | pos |
| 102 | H.haemolyticus 47802/88 | pos |
| 103 | H.haemolyticus 937016 | pos |
| 104 | H.haemolyticus 74108/81 | pos |
| 520 | H. parainfluenzae Biotype I HK 409 | 0 |
| 521 | H. parainfluenzae Biotype II HK 23 | 0 |
| 58 | 59004 H.parainfl.biov.III | 0 |
| 59 | 75834 H.parainfl.biov.III | 0 |
| 60 | 78909 H.parainfl.biov.III | 0 |
| 97 | H. parainfluenzae 947172 | 0 |
| 98 | H. parainfluenzae 59257/91 | 0 |
| 99 | H. parainfluenzae 59004/91 | 0 |
| 100 | H. parainfluenzae 977101 | 0 |
| 545 | H.parainfluenzae Buffalo 3198 NT | 0 |
| 75 | H.somnus CCUG 37617 | 0 |
| 512 | H. parasuis 9918 | 0 |
| 516 | H. parasuis 99 19 | 0 |
| 527 | H. parasuis EF 3712 | 0 |
| 524 | H. paraphrophilus HK 319 | 0 |
| 525 | H. paraphrophilus HK 415 | 0 |
| 517 | H. paraphrophilus 12894 | 0 |
| 71 | H.segnis CCUG 14834 | 0 |
| 526 | H. aphrophilus HK 327 | 0 |
| 529 | H. aphrophilus 11832 A | 0 |
| 532 | H. pleurapneumoniae EF 9917 | 0 |
| 61 | 39612 Eikenella corrodens | 0 |
| 62 | 49064 Eikenella corrodens | 0 |
| 63 | 959074 Eikenella corrodens | 0 |
| 537 | Actinobacillus actinomyc. HK 666 | 0 |
| | P.mult.78908/90 | 0 |

Recombinantly Produced pE22-160 [pE(A)] is Detected by IgD(λ)

In initial experiments, we tried to recombinantly manufacture pE, but only minute concentrations were obtained. To maximize the protein yield, a truncated pE fragment consisting of amino acid residues lysine22 to lysine160 was constructed. The N-terminal signal peptide including the amino acid glutamine21 was thus removed and replaced with the leader peptide in addition to nine residues originating from the vector pET26(+) (FIG. 5A). The truncated pE22-160 was designated pE(A) (FIG. 5B). To confirm that the recombinant protein product corresponded to 'wild type' pE, the recombinantly expressed pE(A) together with pE isolated from NTHi 772 was analysed by SDS-PAGE and Western blot using the IgD(λ) as a probe. As shown in FIG. 5D, the recombinant pE(A) significantly corresponded to wild type pE in SDS-PAGE. Furthermore, pE(A) produced in E. coli could be detected down to 0.01 microg by the IgD(λ) antiserum (FIG. 5E).

pE(A) was used for immunization of rabbits and after completion of the immunization schedule as described in detail in Material and Methods, the anti-pE antiserum was purified on a column consisting of a calculated immunodominant peptide (amino acids pE41-68). The resulting antibodies clearly detected pE both at the bacterial surface (FIG. 2C) and in Western blots (not shown).

The DNA Sequence of the Protein e Gene and the Open Reading Frame

Figure 6:
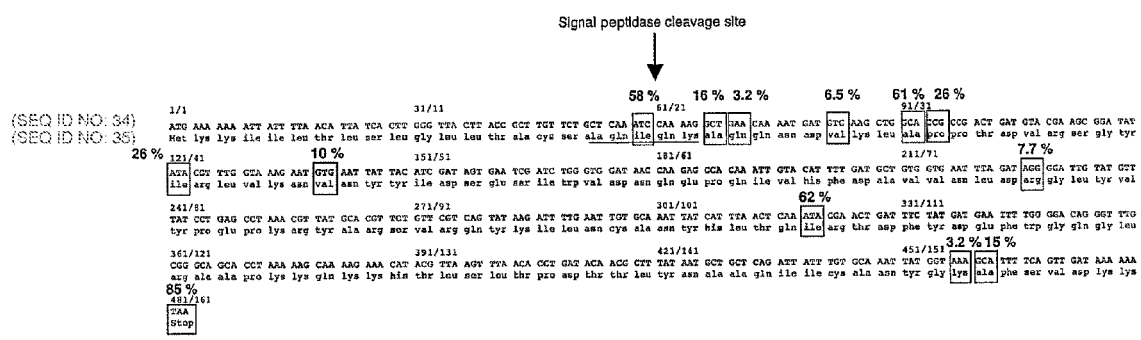
FIG. 6. Protein E is extraordinary conserved. The frequency of point mutations in 13 to 31 *Haemophilus influenzae* strains (Table 2) including both encapsulated and non-typable isolates are shown. Results were obtained by sequencing using flanking primers. All sequences were compared to the pE sequence of *H. influenzae* Rd that was used as a reference sequence and is shown here (the DNA sequence is SEQ ID NO: 34 and the protein sequence is SEQ ID NO: 35).
Figure 7:
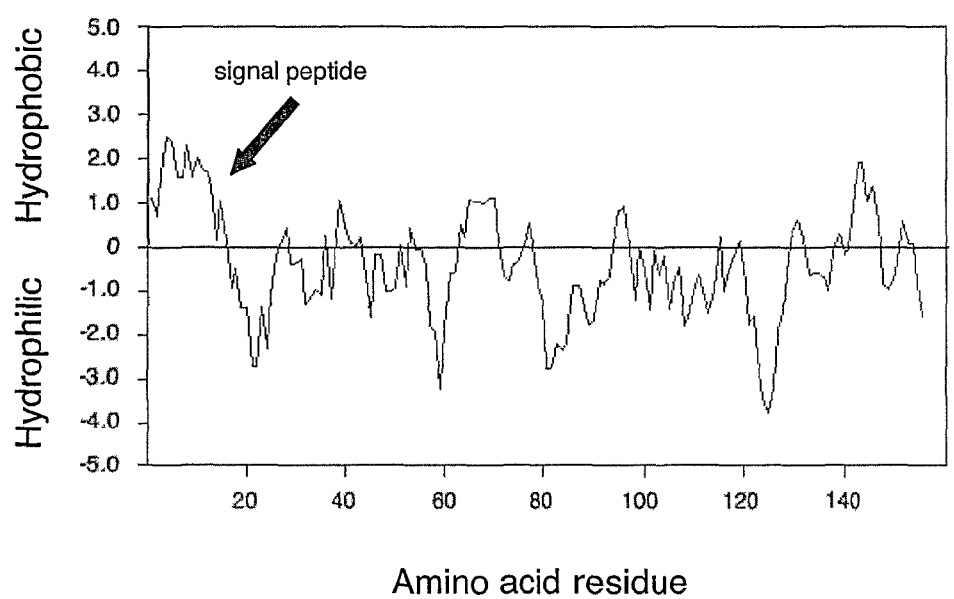
FIG. 7. The hydropathy profile of pE. The hydrophobic and hydrophilic parts of the individual amino acid residues are indicated. The predicted signal peptide is also outlined. Data was obtained by using a standard method as described (21).

The DNA and amino acid sequence of pE1-160 from the strain NTHi 772 is outlined in FIG. 6. The open reading frame (ORF) is 160 amino acids long and the predicted signal peptide has a length of 20 amino acids. Computer analysis suggested that the signal peptidase recognizes the amino acid residues alanine18 to lysine22 and cleaves between residues isoleucine20 and glutamine21 (38). In parallel, the HID hydropathy profile (39) shows that pE has a hydrophobic signal peptide, whereas the rest of the molecule is mainly hydrophilic (FIG. 7).

Figure 5:
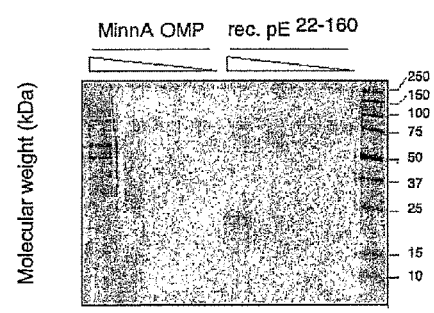
FIG. 5. Recombinant pE22-160 based upon the sequence from NTHi 772 as compared to native pE from *H. influenzae* MinnA. In A, the amino-terminal sequence of the pE-derived fragment A (SEQ ID NO: 32) compared with the predicted amino-terminal sequence of native protein pE (SEQ ID NO: 31). In B, a schematic illustration of pE(A) with the Histidine tag (SEQ ID NO: 12) is shown (MDIGINSDP disclosed as SEQ ID NO: 33). In C, the size and purity is demonstrated on a Commassie-stained PAGE. In D and E, an outer membrane protein (OMP) extract from *H. influenzae* MinnA is compared to recombinantly produced pE(A) in a Coomassie-stained gel and Western Blot, respectively. In A, the signal peptide sequence was removed in addition to the amino acid residue glutamine 21. Nine amino acids were derived from the expression vector pET26(+) as indicated. Numbers represent amino acid positions beginning from the translational start of pE. Recombinant pE(A) was produced in *E. coli*, purified, and subjected to Edman degradation in order to analyse the signal peptidase cleavage site. In D and E, two gels were run simultaneously, one was stained with Coomassie brilliant blue and one was blotted onto Immobilon-P membranes, probed with human IgD(λ) myeloma protein followed by incubation with appropriate horseradish peroxidase-conjugated secondary antibodies. The OMP fraction was purified using Empigen® as described in Material and Methods.
Figure 5:
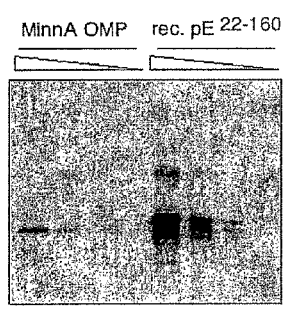

To in detail determine the signal peptidase cleavage site, recombinant full length pE was subjected to Edman degradation. However, the amino-terminal end of the pE polypeptide chain was probably blocked. A possible explanation for this failure could be that the first amino acid was a pyroglutamyl residue as previously described for the M. catarrhalis UspA family of proteins (11). However, attempts to remove this putative residue with pyroglutamate aminopeptidase failed. In contrast to full length pE1-160, the N-terminal sequence for pE(A) (pE22-160) that lacks the endogenous H. influenzae signal peptide (FIG. 5), was successfully characterized by Edman degradation and found to contain the predicted vector sequence, i.e., the signal peptidase in E. coli cleaved at the correct position (FIG. 5A).

Protein E was sequenced in a series of different Haemophilus species including NTHi and encapsulated H. influenzae (Table 1). Interestingly, pE was extraordinary conserved. Only a few amino acids were point mutated and these were mutated in most strains following a specific pattern (FIG. 6 and Table 2).

TABLE 2

Point mutations in the pe gene in different *Haemophilus* species when compared to *H. influenzae* Rd as reference strain[a].

| Point mutation | Number of strains with mutations (%) | Number analysed |
|---|---|---|
| Ile20 > Thr20 | 18 (58%) | 31 |
| Ala23 > Val23 | 5 (16%) | 31 |
| Glu24 > Lys24 | 1[b] (3.2%) | 31 |
| Val28 > Met28 | 2 (6.5%) | 31 |
| Ala31 > Thr31 | 19 (61%) | 31 |
| Pro32 > Val32 | 3 (9.7%) | 31 |
| Pro32 > Ala32 | 5 (16%) | 31 |
| Ile41 > Val41 | 8 (26%) | 31 |
| Val47 > Ala47 | 3 (10%) | 30 |
| Arg76 > Lys76 | 2 (7.7%) | 26 |
| Ile107 > Val107 | 16 (62%) | 26 |
| Lys153 > Glu153 | 1[b] (3.2%) | 13 |
| Ala154 > Val154 | 2 (15%) | 13 |
| Prolonged C-terminal (3 extra aa) | | |
| SVDKK stop (=Rd) [c] (SEQ ID NO: 19) | 11 (85%) | 13 |
| SVDKKSAP stop (SEQ ID NO: 20) | 2 (15%) | 13 |

[a]The pe gene was sequenced in encapsulated *H. influenzae* type a (n = 2), b (n = 2), c (n = 2), d (n = 1), e (n = 2), and f (n = 3), NTHi (n = 8), *H. influenzae* biovar *aegypticus* (n = 6) and *H. aegypticus* (n = 5), using flanking primers.
[b]NTHi 772 (SEQ ID NO: 1)
[c] Rd designates *H. influenzae* strain Rd.

Different Fragments of pE can Easily be Produced in *E. coli*

Eight cDNA sequences derived from the full length pE were cloned into pET26b(+) and expressed in *E. coli*. Resulting proteins were purified on nickel resins with affinity for histidine tags (FIG. 8). The recombinant proteins covered the entire mature pE protein product and their individual lengths and positions were as demonstrated in FIG. 8A and the purified products are outlined in FIG. 8B.

pE is a Crucial Virulence Factor in Rat Acute Otitis Media (AOM)

Figure 9:
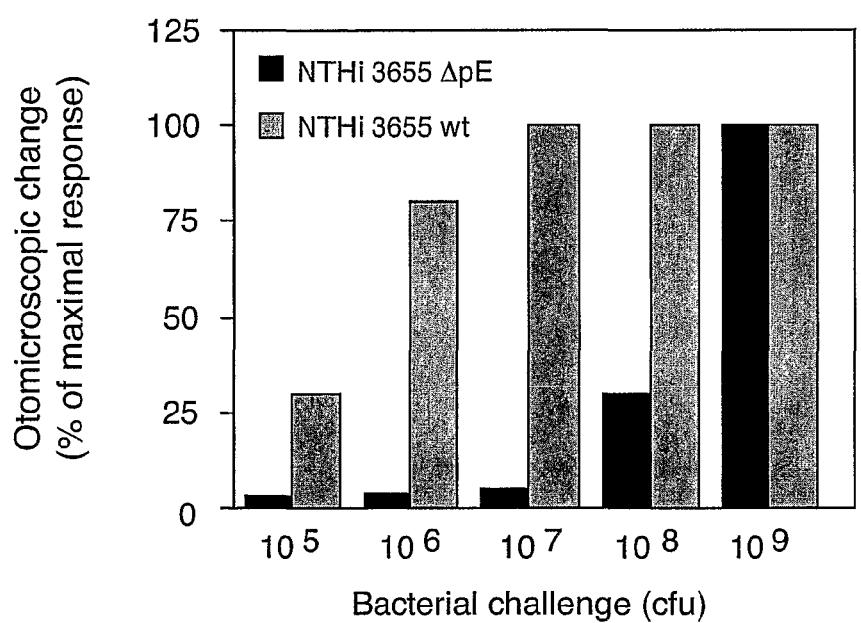
FIG. 9. A pE-deficient mutant strain (NTHi 3655) has a 100 to 1,000-fold lower capacity to induce acute otitis media in rats. Infection was induced in male Sprague-Dawley rats by a ventral midline incision in the neck followed by injection into the middle ear cavity of the indicated numbers of bacteria in 0.05 ml. The data shown is from day 3 of challenge and is representative of five animals in each group.
Figure 10:
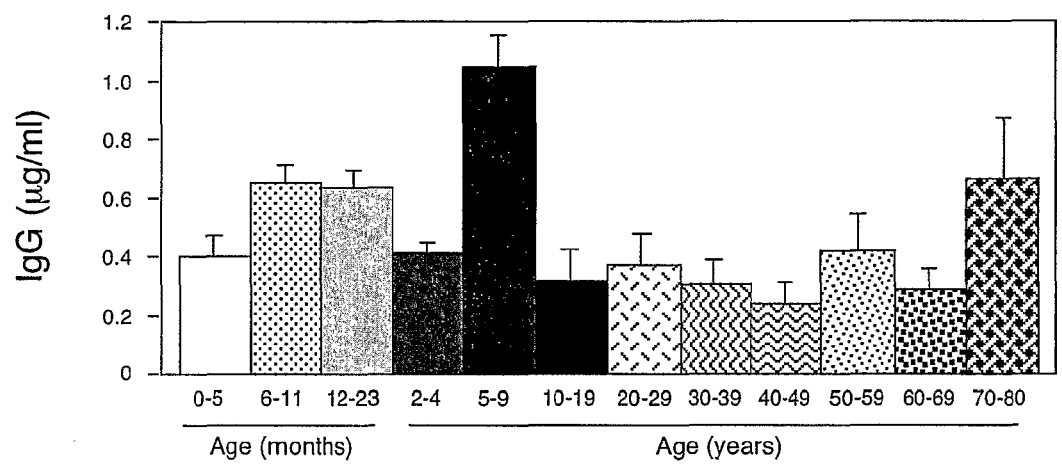
FIG. 10. Mean concentrations of IgG and IgA antibodies directed against pE in sera from different age groups. Anti-pE antibodies were analysed by a sandwich ELISA using recombinant pE(A) as bate. The purity of pE(A) was as indicated in FIG. 5.
Figure 10:
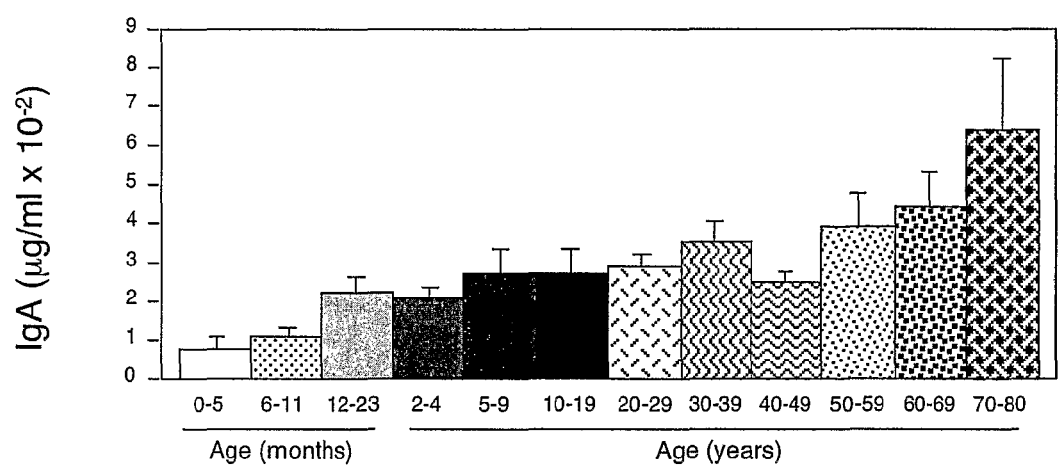

To investigate the role of pE as a virulence factor for NTHi, rats were challenged in the middle ear with $10^5$ to $10^9$ NTHi 3655 Δpe or the corresponding wild type NTHi 3655 (FIG. 9). Interestingly, a 100- to 1,000-fold more of NTHi 3655 Δpe was required in order to induce a similar AOM as compared to the wild type bacterium. Thus, pE is a crucial virulence factor for NTHi-induced AOM.

pE is Highly Immunogenic in a Defined Population

To measure antibody levels in children and blood donors, recombinant pE(A) was purified from *E. coli* (FIG. 5B) and used in an ELISA. The results of ELISA-analyses of antibodies against pE(A) are shown in FIG. 9. Children less than 6 months of age had detectable IgG and IgA against pE(A). IgG antibodies showed peak levels in children of 5 to 10 years of age. In contrast, IgA antibodies increased gradually with increasing age and the highest values were detected in the 70 to 80-year age group.

Useful Epitopes

The B-cell epitopes of a protein are mainly localized at its surface. To predict B-cell epitopes of protein E polypeptides two methods were combined: 2D-structure prediction and antigenic index prediction. The 2D-structure prediction was made using the PSIPRED program (from David Jones, Brunel Bioinformatics Group, Dept. Biological Sciences, Brunel University, Uxbridge UB8 3PH, UK). The antigenic index was calculated on the basis of the method described by Jameson and Wolf (CABIOS 4:181-186 [1988]). The parameters used in this program are the antigenic index and the minimal length for an antigenic peptide. An antigenic index of 0.9 for a minimum of 5 consecutive amino acids was used as threshold in the program. Peptides comprising good, potential B-cell epitopes are listed in table 3. These can be useful (preferably conjugated or recombinantly joined to a larger protein) in a vaccine composition for the prevention of ntHi infections, as could similar peptides comprising conservative mutations (preferably 70, 80, 85, 95, 99 or 100% identical to the sequences of table 3) or truncates comprising 5 or more (e.g. 6, 7, 8, 9, 10, 11, 12, 15, 20 or 25) amino acids therefrom or extensions comprising e. g. 1, 2, 3, 5, 10 further amino acids at N- and/or C-terminal ends of the peptide from the native context of protein E (SEQ ID NO: 1 or natural homologues thereof as shown in Table 2 above) polypeptide which preserve an effective epitope which can elicit an immune response in a host against the protein E polypeptide.

TABLE 3

Potential B-cell epitopes from SEQ ID NO: 1 (or natural homologues thereof)

| Position | Sequence |
|---|---|
| 21 | QKAKQND (SEQ ID NO: 21) |
| 21 | QKVKQND (SEQ ID NO: 22) |
| 21 | QKAQQND (SEQ ID NO: 23) |
| 21 | QKVQQND (SEQ ID NO: 24) |
| 59 | DNQEPQ (SEQ ID NO: 25) |
| 82 | PEPKRYARSVRQ (SEQ ID NO: 26) |
| 106 | QIRTDFYDEFWGQG (SEQ ID NO: 27) |
| 106 | QVRTDFYDEFWGQG (SEQ ID NO: 28) |
| 123 | APKKQKKH (SEQ ID NO: 29) |
| 136 | PDTTL (SEQ ID NO: 30) |

CONCLUSIONS

The surface exposed *Haemophilus* outer membrane protein pE is a crucial virulence factor for NTHi-induced AOM, is highly immunogenic in a defined population and thus is a very suitable vaccine candidate for a variety of human diseases.

REFERENCES

1. Ruan, M., M. Akkoyunlu, A. Grubb, and A. Forsgren. 1990. Protein D of *Haemophilus influenzae*. A novel bacterial surface protein with affinity for human IgD. *J. Immunol.* 145:3379.
2. Janson, H., L.-O. Hedén, A. Grubb, M. Ruan, and A. Forsgren. 1991. Protein D, an immunoglobulin D-binding protein of *Haemophilius influenzae*: cloning, nucleotide sequence, and expression in *Escherichia coli*. *Infect. Immun.* 59:119.
3. Janson, H., Å. Melhus, A. Hermansson, and A. Forsgren. 1994. Protein D, the glycerophosphodiester phosphodiesterase from *Haemophilus influenzae* with affinity for human immunoglobulin D, influences virulence in a rat otitis model. *Infect. Immun.* 62:4848.
4. Janson, H., B. Carlén, A. Cervin, A. Forsgren, A. Björk-Magnusdottir, S. Lindberg, and T. Runer. 1999. Effects on the ciliated epithelium of protein D-producing and -non-producing nontypeable *Haemophilus influenzae* in nasopharyngeal tissue cultures. *J. Infect. Dis.* 180:737.
5. Ahren, I. L., H. Janson, A. Forsgren, K. Riesbeck. 2001. Protein D expression promotes the adherence and internalization of non-typeable *Haemophilus influenzae* into human monocytic cells. *Microb. Pathog.* 31:151.
6. Forsgren, A. and Grubb, A. (1979) Many bacterial species bind human IgD. *J. Immunol.* 122, 1468-1472.
7. Banck, G. and Forsgren, A. (1978) Many bacterial species are mitogenic for human blood lymphocytes. *Scand. J. Immunol.* 8, 347-354.
8. Calvert, J. E. and Calogeres, A. (1986) Characteristics of human B cells responsive to the T-independent mitogen Branhamella *catarrhalis*. *Immunology* 58, 37-41.
9. Forsgren, A., Penta, A., Schlossman, S. F. and Tedder, T. F. (1988) Branhamella *catarrhalis* activates human B lymphocytes following interactions with surface IgD and class I major histocompatibility complex antigens. *Cell. Immunol.* 112, 78-88.
10. Sasaki, K. and Munson Jr., R. S. (1993) Protein D of *Haemophilus influenzae* is not a universal immunoglobulin D-binding protein. *Infect. Immun.* 61, 3026-3031.
11. Forsgren, A., M. Brant, A. Möllenkvist, A. Muyombwe, H. Janson, N. Woin, and K. Riesbeck. 2001. Isolation and characterization of a novel IgD-binding protein from *Moraxella catarrhalis*. *J. Immunol.* 167:2112.
12. Gorg, A., C. Obermaier, G. Boguth, W. Weiss. 1999. Recent developments in two-dimensional gel electrophoresis with immobilized pH gradients: wide pH gradients up to pH 12, longer separation distances and simplified procedures. *Electrophoresis* 20:712.
13. Berns, K. I. and C. A. Thomas, Jr. 1965. Isolation og high molecular weight DNA from *Haemophilus influenzae*. *J. Mol. Biol.* 11:476.
14. Clark-Curtiss, J. E., W. R. Jacobs, M. A. Docherty, L. R. Ritchie, and R. Curtiss, 3rd. 1985. Molecular analysis of DNA and construction of genomic libraries of *Mycobacterium leprae*. *J Bacteriol.* 161:1093.
15. Fleischmann, R. D., M. D. Adams, O. White, R. A. Clayton, E. F. Kirkness, A. R. Kerlavage, C. J. Bult, J. F. Tomb, B. A. Dougherty, J. M. Merrick, et al. 1995. Whole-genome random sequencing and assembly of *Haemophilus influenzae* Rd. *Science* 269:496.
16. Nielsen, H., J. Engelbrecht, S. Brunak, and G. von Heijne. 1997. Identification of prokaryotic and eukaryotic signal peptides and prediction of their cleavage sites. *Protein Engineering* 10: 1.
17. Kyte, J. and R. F. Doolittle. 1982. A simple method for displaying the hydropathic character of a protein. *J. Mol. Biol.* 157:105.
18. Poje, G., and J. R. Redfield. 2003. Transformation of *Haemophilus influenzae*. *Methods. Mol. Med.* 71:57-70.
19. Hussain, M., K. Becker, C. Von Eiff, J. Schrenzel, G. Peters, and M. Herrmann. 2001. *J. Bacteriol.* 183(23): 6778-6786.

The invention claimed is:

1. An immunogenic composition comprising an isolated polypeptide, wherein the polypeptide comprises an amino acid sequence that varies from SEQ ID NO:1 in at least three positions, wherein the variation(s) are selected from the group consisting of a deletion of a signal peptide (amino acids 1-20) of SEQ ID NO:1, a Thr substitution of Ile at position 20 of SEQ ID NO:1, a Val substitution of Ala at position 23 of SEQ ID NO:1, a Glu substitution of Lys at position 24 of SEQ ID NO:1, a Met substitution of Val at position 28 of SEQ ID NO:1, a Thr substitution of Ala at position 31 of SEQ ID NO:1, a Val substitution of Ile at position 41 of SEQ ID NO:1, an Ala substitution of Val at position 47 of SEQ ID NO:1, a Lys substitution of Arg at position 76 of SEQ ID NO:1, a Val substitution of Ile at position 107 of SEQ ID NO:1, a Lys substitution of Gly at position 152 of SEQ ID NO:1, a Val substitution of Ala at position 154 of SEQ ID NO:1, a Ser-Ala-Pro addition at the C-terminus of SEQ ID NO:1, a Val substitution of Pro at position 32 of SEQ ID NO:1, and an Ala substitution of Pro at position 32 of SEQ ID NO:1, wherein the composition further comprises an immunogenic portion of an outer membrane protein of a respiratory tract pathogen.

2. An immunogenic composition comprising an isolated polypeptide, wherein the polypeptide comprises an amino acid sequence that varies from SEQ ID NO:1 in at least three positions, wherein the variation(s) are selected from the group consisting of a deletion of a signal peptide (amino acids 1-20) of SEQ ID NO:1, a Thr substitution of Ile at position 20 of SEQ ID NO:1, a Val substitution of Ala at position 23 of SEQ ID NO:1, a Glu substitution of Lys at position 24 of SEQ ID NO:1, a Met substitution of Val at position 28 of SEQ ID NO:1, a Thr substitution of Ala at position 31 of SEQ ID NO:1, a Val substitution of Ile at position 41 of SEQ ID NO:1, an Ala substitution of Val at position 47 of SEQ ID NO:1, a Lys substitution of Arg at position 76 of SEQ ID NO:1, a Val substitution of Ile at position 107 of SEQ ID NO:1, a Lys substitution of Gly at position 152 of SEQ ID NO:1, a Val substitution of Ala at position 154 of SEQ ID NO:1, a Ser-Ala-Pro addition at the C-terminus of SEQ ID NO:1, a Val substitution of Pro at position 32 of SEQ ID NO:1, and an Ala substitution of Pro at position 32 of SEQ ID NO:1, wherein the composition further comprises an immunogenic portion of a molecule selected from the group consisting of pneumolysin from *Streptococcus pneumoniae*; IgD binding protein (MID), outer membrane protein (Omp)106, ubiquitous surface protein (Usp) A1, UspA2, hemolysin (Hly3), OmpCD, and D15 from *Moraxella catarrhalis*; and Omp26, P6, Protein D, new lipoprotein (Nlp) C2, and synaptotagmin-like protein (Sip) from *Haemophilus influenza*.

3. An immunogenic composition comprising an isolated polypeptide, wherein the polypeptide comprises an amino acid sequence that varies from SEQ ID NO:1 in at least three positions, wherein the variation(s) are selected from the group consisting of a deletion of a signal peptide (amino acids 1-20) of SEQ ID NO:1, a Thr substitution of Ile at position 20 of SEQ ID NO:1, a Val substitution of Ala at position 23 of SEQ ID NO:1, a Glu substitution of Lys at position 24 of SEQ ID NO:1, a Met substitution of Val at position 28 of SEQ ID NO:1, a Thr substitution of Ala at position 31 of SEQ ID NO:1, a Val substitution of Ile at position 41 of SEQ ID NO:1, an Ala substitution of Val at position 47 of SEQ ID NO:1, a Lys substitution of Arg at position 76 of SEQ ID NO:1, a Val substitution of Ile at position 107 of SEQ ID NO:1, a Lys substitution of Gly at position 152 of SEQ ID NO:1, a Val substitution of Ala at position 154 of SEQ ID NO:1, a Ser-Ala-Pro addition at the C-terminus of SEQ ID NO:1, a Val substitution of Pro at position 32 of SEQ ID NO:1, and an Ala substitution of Pro at position 32 of SEQ ID NO:1, and wherein the polypeptide is fused recombinantly with at least another protein.

4. An immunogenic composition comprising an isolated polypeptide, wherein the polypeptide comprises an amino acid sequence that varies from SEQ ID NO:1 in at least three positions, wherein the variation(s) are selected from the group consisting of a deletion of a signal peptide (amino acids 1-20) of SEQ ID NO:1, a Thr substitution of Ile at position 20 of SEQ ID NO:1, a Val substitution of Ala at position 23 of SEQ ID NO:1, a Glu substitution of Lys at position 24 of SEQ ID NO:1, a Met substitution of Val at position 28 of SEQ ID NO:1, a Thr substitution of Ala at position 31 of SEQ ID NO:1, a Val substitution of Ile at position 41 of SEQ ID NO:1, an Ala substitution of Val at position 47 of SEQ ID NO:1, a Lys substitution of Arg at position 76 of SEQ ID NO:1, a Val substitution of Ile at position 107 of SEQ ID NO:1, a Lys substitution of Gly at position 152 of SEQ ID NO:1, a Val substitution of Ala at position 154 of SEQ ID NO:1, a Ser-Ala-Pro addition at the C-terminus of SEQ ID NO:1, a Val substitution of Pro at position 32 of SEQ ID NO:1, and an Ala substitution of Pro at position 32 of SEQ ID NO:1, and wherein the polypeptide is covalently or non-covalently bound to a protein, carbohydrate, or matrix.

* * * * *

```
                     SEQUENCE LISTING

<160> NUMBER OF SEQ ID NOS: 62

<210> SEQ ID NO 1
<211> LENGTH: 160
<212> TYPE: PRT
<213> ORGANISM: Haemophilus influenzae

<400> SEQUENCE: 1

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Arg Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160

<210> SEQ ID NO 2
<211> LENGTH: 139
<212> TYPE: PRT
<213> ORGANISM: Haemophilus influenzae
```

```
<400> SEQUENCE: 2

Lys Ala Lys Gln Asn Asp Val Lys Leu Ala Pro Pro Thr Asp Val Arg
1               5                   10                  15

Ser Gly Tyr Ile Arg Leu Val Lys Asn Val Asn Tyr Tyr Ile Asp Ser
            20                  25                  30

Glu Ser Ile Trp Val Asp Asn Gln Glu Pro Gln Ile Val His Phe Asp
        35                  40                  45

Ala Val Val Asn Leu Asp Arg Gly Leu Tyr Val Tyr Pro Glu Pro Lys
    50                  55                  60

Arg Tyr Ala Arg Ser Val Arg Gln Tyr Lys Ile Leu Asn Cys Ala Asn
65              70                  75                  80

Tyr His Leu Thr Gln Ile Arg Thr Asp Phe Tyr Asp Glu Phe Trp Gly
            85                  90                  95

Gln Gly Leu Arg Ala Ala Pro Lys Lys Gln Lys Lys His Thr Leu Ser
        100                 105                 110

Leu Thr Pro Asp Thr Thr Leu Tyr Asn Ala Ala Gln Ile Ile Cys Ala
            115                 120                 125

Asn Tyr Gly Glu Ala Phe Ser Val Asp Lys Lys
    130                 135

<210> SEQ ID NO 3
<211> LENGTH: 28
<212> TYPE: PRT
<213> ORGANISM: Haemophilus influenzae

<400> SEQUENCE: 3

Ile Arg Leu Val Lys Asn Val Asn Tyr Tyr Ile Asp Ser Glu Ser Ile
1               5                   10                  15

Trp Val Asp Asn Gln Glu Pro Gln Ile Val His Phe
            20                  25

<210> SEQ ID NO 4
<211> LENGTH: 39
<212> TYPE: PRT
<213> ORGANISM: Haemophilus influenzae

<400> SEQUENCE: 4

Lys Ala Lys Gln Asn Asp Val Lys Leu Ala Pro Pro Thr Asp Val Arg
1               5                   10                  15

Ser Gly Tyr Ile Arg Leu Val Lys Asn Val Asn Tyr Tyr Ile Asp Ser
            20                  25                  30

Glu Ser Ile Trp Val Asp Asn
        35

<210> SEQ ID NO 5
<211> LENGTH: 74
<212> TYPE: PRT
<213> ORGANISM: Haemophilus influenzae

<400> SEQUENCE: 5

Lys Ala Lys Gln Asn Asp Val Lys Leu Ala Pro Pro Thr Asp Val Arg
1               5                   10                  15

Ser Gly Tyr Ile Arg Leu Val Lys Asn Val Asn Tyr Tyr Ile Asp Ser
            20                  25                  30

Glu Ser Ile Trp Val Asp Asn Gln Glu Pro Gln Ile Val His Phe Asp
        35                  40                  45

Ala Val Val Asn Leu Asp Arg Gly Leu Tyr Val Tyr Pro Glu Pro Lys
    50                  55                  60
```

```
Arg Tyr Ala Arg Ser Val Arg Gln Tyr Lys
 65                  70
```

```
<210> SEQ ID NO 6
<211> LENGTH: 104
<212> TYPE: PRT
<213> ORGANISM: Haemophilus influenzae

<400> SEQUENCE: 6

Lys Ala Lys Gln Asn Asp Val Lys Leu Ala Pro Pro Thr Asp Val Arg
  1               5                  10                  15

Ser Gly Tyr Ile Arg Leu Val Lys Asn Val Asn Tyr Tyr Ile Asp Ser
             20                  25                  30

Glu Ser Ile Trp Val Asp Asn Gln Glu Pro Gln Ile Val His Phe Asp
         35                  40                  45

Ala Val Val Asn Leu Asp Arg Gly Leu Tyr Val Tyr Pro Glu Pro Lys
     50                  55                  60

Arg Tyr Ala Arg Ser Val Arg Gln Tyr Lys Ile Leu Asn Cys Ala Asn
 65                  70                  75                  80

Tyr His Leu Thr Gln Ile Arg Thr Asp Phe Tyr Asp Glu Phe Trp Gly
                 85                  90                  95

Gln Gly Leu Arg Ala Ala Pro Lys
            100
```

```
<210> SEQ ID NO 7
<211> LENGTH: 70
<212> TYPE: PRT
<213> ORGANISM: Haemophilus influenzae

<400> SEQUENCE: 7

Ile Trp Val Asp Asn Gln Glu Pro Gln Ile Val His Phe Asp Ala Val
  1               5                  10                  15

Val Asn Leu Asp Arg Gly Leu Tyr Val Tyr Pro Glu Pro Lys Arg Tyr
             20                  25                  30

Ala Arg Ser Val Arg Gln Tyr Lys Ile Leu Asn Cys Ala Asn Tyr His
         35                  40                  45

Leu Thr Gln Ile Arg Thr Asp Phe Tyr Asp Glu Phe Trp Gly Gln Gly
     50                  55                  60

Leu Arg Ala Ala Pro Lys
 65                  70
```

```
<210> SEQ ID NO 8
<211> LENGTH: 105
<212> TYPE: PRT
<213> ORGANISM: Haemophilus influenzae

<400> SEQUENCE: 8

Ile Trp Val Asp Asn Gln Glu Pro Gln Ile Val His Phe Asp Ala Val
  1               5                  10                  15

Val Asn Leu Asp Arg Gly Leu Tyr Val Tyr Pro Glu Pro Lys Arg Tyr
             20                  25                  30

Ala Arg Ser Val Arg Gln Tyr Lys Ile Leu Asn Cys Ala Asn Tyr His
         35                  40                  45

Leu Thr Gln Ile Arg Thr Asp Phe Tyr Asp Glu Phe Trp Gly Gln Gly
     50                  55                  60

Leu Arg Ala Ala Pro Lys Lys Gln Lys Lys His Thr Leu Ser Leu Thr
 65                  70                  75                  80
```

```
Pro Asp Thr Thr Leu Tyr Asn Ala Ala Gln Ile Ile Cys Ala Asn Tyr
                85                  90                  95

Gly Glu Ala Phe Ser Val Asp Lys Lys
        100                 105

<210> SEQ ID NO 9
<211> LENGTH: 75
<212> TYPE: PRT
<213> ORGANISM: Haemophilus influenzae

<400> SEQUENCE: 9

Arg Tyr Ala Arg Ser Val Arg Gln Tyr Lys Ile Leu Asn Cys Ala Asn
1               5                   10                  15

Tyr His Leu Thr Gln Ile Arg Thr Asp Phe Tyr Asp Glu Phe Trp Gly
            20                  25                  30

Gln Gly Leu Arg Ala Ala Pro Lys Lys Gln Lys Lys His Thr Leu Ser
        35                  40                  45

Leu Thr Pro Asp Thr Thr Leu Tyr Asn Ala Ala Gln Ile Ile Cys Ala
    50                  55                  60

Asn Tyr Gly Glu Ala Phe Ser Val Asp Lys Lys
65                  70                  75

<210> SEQ ID NO 10
<211> LENGTH: 46
<212> TYPE: PRT
<213> ORGANISM: Haemophilus influenzae

<400> SEQUENCE: 10

Phe Trp Gly Gln Gly Leu Arg Ala Ala Pro Lys Lys Gln Lys Lys His
1               5                   10                  15

Thr Leu Ser Leu Thr Pro Asp Thr Thr Leu Tyr Asn Ala Ala Gln Ile
            20                  25                  30

Ile Cys Ala Asn Tyr Gly Glu Ala Phe Ser Val Asp Lys Lys
        35                  40                  45

<210> SEQ ID NO 11
<211> LENGTH: 483
<212> TYPE: DNA
<213> ORGANISM: Haemophilus influenzae

<400> SEQUENCE: 11
atgaaaaaaa ttattttaac attatcactt gggttactta ctgcctgttc tgctcaaatc     60
caaaaggcta acaaaatga tgtgaagctg gcaccgccga ctgatgtacg aagcggatat    120
atacgtttgg taagaatgt gaattattac atcgatagtg aatcgatctg ggtggataac    180
caagagccac aaattgtaca ttttgatgca gtggtgaatt tagatagggg attgtatgtt    240
tatcctgagc ctaaacgtta tgcacgttct gttcgtcagt ataagatctt gaattgtgca    300
aattatcatt taactcaaat acgaactgat ttctatgatg aatttggggg acagggtttg    360
cgggcagcac ctaaaaagca aagaaacat acgttaagtt taacacctga taacgcttct    420
tataatgctg ctcagattat ttgtgcgaac tatggtgaag catttcagt tgataaaaaa    480 taa                                                                 483

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
```

6xHis tag

<400> SEQUENCE: 12

His His His His His His
1               5

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctcaggatcc aaaggctgaa caaaatgatg tg                                    32

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggtgcagatt aagctttttt ttatcaactg                                       30

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcatttatta ggtcagttta ttg                                              23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaaggattat ttctgatgca g                                                21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cttgggttac ttaccgcttg                                                  20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic

```
                      primer

<400> SEQUENCE: 18
gtgttaaact taacgtatg                                                  19

<210> SEQ ID NO 19
<211> LENGTH: 5
<212> TYPE: PRT
<213> ORGANISM: Haemophilus influenzae

<400> SEQUENCE: 19

Ser Val Asp Lys Lys
1               5

<210> SEQ ID NO 20
<211> LENGTH: 8
<212> TYPE: PRT
<213> ORGANISM: Haemophilus influenzae

<400> SEQUENCE: 20

Ser Val Asp Lys Lys Ser Ala Pro
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Lys Ala Lys Gln Asn Asp
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Lys Val Lys Gln Asn Asp
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Lys Ala Gln Gln Asn Asp
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 24

Gln Lys Val Gln Gln Asn Asp
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asn Gln Glu Pro Gln
1               5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Glu Pro Lys Arg Tyr Ala Arg Ser Val Arg Gln
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Ile Arg Thr Asp Phe Tyr Asp Glu Phe Trp Gly Gln Gly
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Val Arg Thr Asp Phe Tyr Asp Glu Phe Trp Gly Gln Gly
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Pro Lys Lys Gln Lys Lys His
1               5

<210> SEQ ID NO 30
<211> LENGTH: 5
<212> TYPE: PRT

-continued

<213> ORGANISM: Artificial Sequence
<220> FEATURE:
<223> OTHER INFORMATION: Description of Artificial Sequence: Synthetic
      peptide

<400> SEQUENCE: 30

Pro Asp Thr Thr Leu
1               5

<210> SEQ ID NO 31
<211> LENGTH: 30
<212> TYPE: PRT
<213> ORGANISM: Haemophilus influenzae

<400> SEQUENCE: 31

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu
            20                  25                  30

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met Asp Ile Gly Ile Asn Ser Asp Pro Lys Ala Lys Gln Asn Asp Val
1               5                   10                  15

Lys Leu

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Asp Ile Gly Ile Asn Ser Asp Pro
1               5

<210> SEQ ID NO 34
<211> LENGTH: 483
<212> TYPE: DNA
<213> ORGANISM: Haemophilus influenzae
<220> FEATURE:
<221> NAME/KEY: CDS
<222> LOCATION: (1)..(480)

<400> SEQUENCE: 34 atg aaa aaa att att tta aca tta tca ctt ggg tta ctt acc gct tgt      48
Met Lys Lys Ile Ile Leu Thr Leu Ser Leu Gly Leu Leu Thr Ala Cys
1               5                   10                  15 tct gct caa atc caa aag gct gaa caa aat gat gtg aag ctg gca ccg      96
Ser Ala Gln Ile Gln Lys Ala Glu Gln Asn Asp Val Lys Leu Ala Pro
            20                  25                  30 ccg act gat gta cga agc gga tat ata cgt ttg gta aag aat gtg aat     144
Pro Thr Asp Val Arg Ser Gly Tyr Ile Arg Leu Val Lys Asn Val Asn
        35                  40                  45 tat tac atc gat agt gaa tcg atc tgg gtg gat aac caa gag cca caa     192
Tyr Tyr Ile Asp Ser Glu Ser Ile Trp Val Asp Asn Gln Glu Pro Gln

| | | | | | | | | | | | | | | | | |
|---|---|---|---|---|---|---|---|---|---|---|---|---|---|---|---|---|
| | | 50 | | | | 55 | | | | 60 | | | | | | |
| att | gta | cat | ttt | gat | gct | gtg | gtg | aat | tta | gat | agg | gga | ttg | tat | gtt | 240 |
| Ile | Val | His | Phe | Asp | Ala | Val | Val | Asn | Leu | Asp | Arg | Gly | Leu | Tyr | Val | |
| 65 | | | | 70 | | | | | 75 | | | | | 80 | | |
| tat | cct | gag | cct | aaa | cgt | tat | gca | cgt | tct | gtt | cgt | cag | tat | aag | att | 288 |
| Tyr | Pro | Glu | Pro | Lys | Arg | Tyr | Ala | Arg | Ser | Val | Arg | Gln | Tyr | Lys | Ile | |
| | | | | 85 | | | | | 90 | | | | | 95 | | |
| ttg | aat | tgt | gca | aat | tat | cat | tta | act | caa | ata | cga | act | gat | ttc | tat | 336 |
| Leu | Asn | Cys | Ala | Asn | Tyr | His | Leu | Thr | Gln | Ile | Arg | Thr | Asp | Phe | Tyr | |
| | | | 100 | | | | | 105 | | | | | 110 | | | |
| gat | gaa | ttt | tgg | gga | cag | ggt | ttg | cgg | gca | gca | cct | aaa | aag | caa | aag | 384 |
| Asp | Glu | Phe | Trp | Gly | Gln | Gly | Leu | Arg | Ala | Ala | Pro | Lys | Lys | Gln | Lys | |
| | | | | 115 | | | | | 120 | | | | | 125 | | |
| aaa | cat | acg | tta | agt | tta | aca | cct | gat | aca | acg | ctt | tat | aat | gct | gct | 432 |
| Lys | His | Thr | Leu | Ser | Leu | Thr | Pro | Asp | Thr | Thr | Leu | Tyr | Asn | Ala | Ala | |
| | | 130 | | | | | 135 | | | | | 140 | | | | |
| cag | att | att | tgt | gca | aat | tat | ggt | aaa | gca | ttt | tca | gtt | gat | aaa | aaa | 480 |
| Gln | Ile | Ile | Cys | Ala | Asn | Tyr | Gly | Lys | Ala | Phe | Ser | Val | Asp | Lys | Lys | |
| 145 | | | | 150 | | | | | 155 | | | | | 160 | | |

```
taa                                                                                483
```

<210> SEQ ID NO 35
<211> LENGTH: 160
<212> TYPE: PRT
<213> ORGANISM: Haemophilus influenzae

<400> SEQUENCE: 35

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Arg Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 36
<211> LENGTH: 160
<212> TYPE: PRT
<213> ORGANISM: Haemophilus influenzae

<400> SEQUENCE: 36

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

```
Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
 50                  55                  60

Ile Val His Phe Asp Ala Val Asn Leu Asp Arg Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
               100                 105                 110

Asp Glu Phe Trp Gly Gln Gly Leu Arg Ala Ala Pro Lys Lys Gln Lys
               115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Lys Ala Phe Ser Val Asp Lys Lys
145                 150                 155                 160

<210> SEQ ID NO 37
<211> LENGTH: 150
<212> TYPE: PRT
<213> ORGANISM: Haemophilus influenzae

<400> SEQUENCE: 37

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
 50                  55                  60

Ile Val His Phe Asp Thr Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
               100                 105                 110

Asp Glu Phe Trp Gly Gln Gly Leu Arg Ala Ala Pro Lys Lys Gln Lys
               115                 120                 125

Lys His Thr Leu Ser Leu Thr Pro Asp Thr Thr Leu Tyr Asn Ala Ala
130                 135                 140

Gln Ile Ile Cys Ala Asn
145                 150

<210> SEQ ID NO 38
<211> LENGTH: 144
<212> TYPE: PRT
<213> ORGANISM: Haemophilus influenzae

<400> SEQUENCE: 38

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
            35                  40                  45
```

```
Tyr Tyr Ile Asp Ser Glu Ser Ile Trp Val Asp Asn Gln Glu Pro Gln
        50                  55                  60

Ile Val His Phe Asp Ala Val Val Asn Leu Asp Arg Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
        130                 135                 140

<210> SEQ ID NO 39
<211> LENGTH: 150
<212> TYPE: PRT
<213> ORGANISM: Haemophilus influenzae

<400> SEQUENCE: 39

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Val Lys Leu Ala Pro
                20                  25                  30

Pro Thr Asp Val Arg Ser Gly Tyr Ile Arg Leu Val Lys Asn Val Asn
                35                  40                  45

Tyr Tyr Ile Asp Ser Glu Ser Ile Trp Val Asp Asn Gln Glu Pro Gln
        50                  55                  60

Ile Val His Phe Asp Ala Val Val Asn Leu Asp Arg Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
        130                 135                 140

Gln Ile Ile Cys Ala Asn
145                 150

<210> SEQ ID NO 40
<211> LENGTH: 148
<212> TYPE: PRT
<213> ORGANISM: Haemophilus aegypticus

<400> SEQUENCE: 40

Met Lys Lys Ile Ile Leu Thr Leu Ser Leu Gly Leu Leu Thr Ala Cys
 1               5                  10                  15

Ser Ala Gln Thr Gln Lys Ala Glu Gln Asn Asp Val Lys Leu Thr Pro
                20                  25                  30

Pro Thr Asp Val Arg Ser Gly Tyr Ile Arg Leu Val Lys Asn Val Asn
                35                  40                  45

Tyr Tyr Ile Asp Ser Glu Ser Ile Trp Val Asp Asn Gln Glu Pro Gln
        50                  55                  60

Ile Val His Phe Asp Ala Val Val Asn Leu Asp Lys Gly Leu Tyr Val
 65                  70                  75                  80
```

```
Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys
145

<210> SEQ ID NO 41
<211> LENGTH: 155
<212> TYPE: PRT
<213> ORGANISM: Haemophilus aegypticus

<400> SEQUENCE: 41

Met Lys Lys Ile Ile Leu Thr Leu Ser Leu Gly Leu Leu Thr Ala Cys
1               5                   10                  15

Ser Ala Gln Thr Gln Lys Ala Glu Gln Asn Asp Val Lys Leu Thr Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe
145                 150                 155

<210> SEQ ID NO 42
<211> LENGTH: 163
<212> TYPE: PRT
<213> ORGANISM: Haemophilus influenzae

<400> SEQUENCE: 42

Met Lys Lys Ile Ile Leu Thr Leu Ser Leu Gly Leu Leu Thr Ala Cys
1               5                   10                  15

Ser Ala Gln Thr Gln Lys Ala Glu Gln Asn Asp Val Lys Leu Thr Val
            20                  25                  30

Pro Thr Asp Val Arg Ser Gly Tyr Val Arg Leu Val Lys Asn Ala Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95
```

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Leu Tyr Asn Ala Ala
    130                 135                 140

Gln Ile Ile Cys Ala Asn Tyr Gly Lys Val Phe Ser Val Asp Lys Lys
145                 150                 155                 160

Ser Ala Pro

<210> SEQ ID NO 43
<211> LENGTH: 160
<212> TYPE: PRT
<213> ORGANISM: Haemophilus aegypticus

<400> SEQUENCE: 43

Met Lys Lys Asn Tyr Phe Asn Ile Ile Thr Gly Leu Leu Thr Ala Cys
1               5                   10                  15

Ser Ala Gln Thr Gln Lys Ala Glu Gln Asn Asp Val Lys Leu Thr Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Leu Tyr Asn Ala Ala
    130                 135                 140

Gln Ile Ile Cys Ala Asn Tyr Gly Lys Ala Phe Ser Val Asp Lys Lys
145                 150                 155                 160

<210> SEQ ID NO 44
<211> LENGTH: 148
<212> TYPE: PRT
<213> ORGANISM: Haemophilus aegypticus

<400> SEQUENCE: 44

Met Lys Lys Ile Ile Leu Thr Leu Ser Leu Gly Leu Leu Thr Ala Cys
1               5                   10                  15

Ser Ala Leu Lys Leu Lys Ala Glu Gln Asn Asp Val Lys Leu Thr Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

```
Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
            130                 135                 140

Gln Ile Ile Cys
145

<210> SEQ ID NO 45
<211> LENGTH: 160
<212> TYPE: PRT
<213> ORGANISM: Haemophilus influenzae

<400> SEQUENCE: 45

Met Lys Lys Ile Ile Leu Thr Leu Ser Leu Gly Leu Leu Thr Ala Cys
1               5                   10                  15

Ser Ala Gln Thr Gln Lys Ala Glu Gln Asn Asp Val Lys Leu Thr Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
            130                 135                 140

Gln Ile Ile Cys Ala Asn Tyr Gly Lys Ala Phe Ser Val Asp Lys Lys
145                 150                 155                 160

<210> SEQ ID NO 46
<211> LENGTH: 148
<212> TYPE: PRT
<213> ORGANISM: Haemophilus influenzae

<400> SEQUENCE: 46

Met Lys Lys Ile Ile Leu Thr Leu Ser Leu Gly Leu Leu Thr Ala Cys
1               5                   10                  15

Ser Ala Gln Thr Gln Lys Ala Glu Gln Asn Asp Val Lys Leu Thr Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Arg Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110
```

```
Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
        130                 135                 140

Gln Ile Ile Cys
145

<210> SEQ ID NO 47
<211> LENGTH: 147
<212> TYPE: PRT
<213> ORGANISM: Haemophilus influenzae

<400> SEQUENCE: 47

Met Lys Lys Ile Ile Leu Thr Leu Ser Leu Gly Leu Leu Thr Ala Cys
1               5                   10                  15

Ser Ala Gln Thr Gln Lys Ala Glu Gln Asn Asp Val Lys Leu Thr Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile
145

<210> SEQ ID NO 48
<211> LENGTH: 158
<212> TYPE: PRT
<213> ORGANISM: Haemophilus influenzae

<400> SEQUENCE: 48

Met Lys Lys Ile Ile Leu Thr Leu Ser Leu Gly Leu Leu Thr Ala Cys
1               5                   10                  15

Ser Ala Gln Thr Gln Lys Ala Glu Gln Asn Asp Val Lys Leu Thr Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Pro Lys Lys Gln Lys Lys His
        115                 120                 125
```

```
Thr Leu Ser Leu Thr Pro Asp Thr Thr Leu Tyr Asn Ala Ala Gln Ile
    130                 135                 140

Ile Cys Ala Asn Tyr Gly Lys Ala Phe Ser Val Asp Lys Lys
145                 150                 155
```

<210> SEQ ID NO 49
<211> LENGTH: 160
<212> TYPE: PRT
<213> ORGANISM: Haemophilus influenzae

<400> SEQUENCE: 49

```
Met Lys Lys Ile Ile Leu Thr Leu Ser Leu Gly Leu Leu Thr Ala Cys
1               5                   10                  15

Ser Ala Gln Thr Gln Lys Val Glu Gln Asn Asp Val Lys Leu Thr Ala
            20                  25                  30

Pro Thr Asp Val Arg Ser Gly Tyr Val Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Arg Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Lys Ala Phe Ser Val Asp Lys Lys
145                 150                 155                 160
```

<210> SEQ ID NO 50
<211> LENGTH: 160
<212> TYPE: PRT
<213> ORGANISM: Haemophilus influenzae

<400> SEQUENCE: 50

```
Met Lys Lys Ile Ile Leu Thr Leu Ser Leu Gly Leu Leu Thr Ala Cys
1               5                   10                  15

Ser Ala Gln Thr Gln Lys Val Glu Gln Asn Asp Val Lys Leu Thr Ala
            20                  25                  30

Pro Thr Asp Val Arg Ser Gly Tyr Val Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140
```

```
Gln Ile Ile Cys Ala Asn Tyr Gly Lys Ala Phe Ser Val Asp Lys Lys
145                 150                 155                 160
```

<210> SEQ ID NO 51
<211> LENGTH: 143
<212> TYPE: PRT
<213> ORGANISM: Haemophilus influenzae

<400> SEQUENCE: 51

```
Met Lys Lys Ile Ile Leu Thr Leu Ser Leu Gly Leu Leu Thr Ala Cys
1               5                   10                  15

Ser Ala Gln Thr Gln Lys Val Glu Gln Asn Asp Val Lys Leu Thr Ala
            20                  25                  30

Pro Thr Asp Val Arg Ser Gly Tyr Val Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala
    130                 135                 140
```

<210> SEQ ID NO 52
<211> LENGTH: 127
<212> TYPE: PRT
<213> ORGANISM: Haemophilus influenzae

<400> SEQUENCE: 52

```
Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln
        115                 120                 125
```

<210> SEQ ID NO 53
<211> LENGTH: 160
<212> TYPE: PRT
<213> ORGANISM: Haemophilus influenzae
<220> FEATURE:
<221> NAME/KEY: MOD_RES
<222> LOCATION: (134)..(134)
<223> OTHER INFORMATION: Any amino acid

```
<220> FEATURE:
<221> NAME/KEY: MOD_RES
<222> LOCATION: (155)..(155)
<223> OTHER INFORMATION: Any amino acid

<400> SEQUENCE: 53

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Xaa Thr Pro Asp Thr Thr Leu Tyr Asn Ala Ala
130                 135                 140

Gln Ile Ile Cys Ala Asn Tyr Gly Lys Ala Xaa Ser Val Asp Lys Lys
145                 150                 155                 160

<210> SEQ ID NO 54
<211> LENGTH: 158
<212> TYPE: PRT
<213> ORGANISM: Haemophilus influenzae

<400> SEQUENCE: 54

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Arg Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
130                 135                 140

Gln Ile Ile Cys Ala Asn Tyr Gly Lys Ala Phe Ser Val Asp
145                 150                 155

<210> SEQ ID NO 55
<211> LENGTH: 154
<212> TYPE: PRT
```

<213> ORGANISM: Haemophilus influenzae

<400> SEQUENCE: 55

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
            85                  90                  95

Leu Asn Cys Ala Asn Tyr His Leu Thr Gln Ile Arg Thr Asp Phe Tyr
        100                 105                 110

Asp Glu Phe Trp Gly Gln Gly Leu Arg Ala Ala Pro Lys Lys Gln
    115                 120                 125

Lys Lys His Thr Leu Ser Leu Thr Pro Asp Thr Thr Leu Tyr Asn Ala
130                 135                 140

Ala Gln Ile Ile Cys Ala Asn Tyr Gly Lys
145                 150

<210> SEQ ID NO 56
<211> LENGTH: 140
<212> TYPE: PRT
<213> ORGANISM: Haemophilus influenzae

<400> SEQUENCE: 56

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Arg Gly Leu Tyr Val
65                  70                  75                  80

Tyr Pro Glu Pro Lys Arg Tyr Ala Arg Ser Val Arg Gln Tyr Lys Ile
            85                  90                  95

Leu Asn Cys Ala Asn Tyr His Leu Thr Gln Ile Arg Thr Asp Phe Tyr
        100                 105                 110

Asp Glu Phe Trp Gly Gln Gly Leu Arg Ala Ala Pro Lys Lys Gln Lys
    115                 120                 125

Lys His Thr Leu Ser Leu Thr Pro Asp Thr Thr Leu
130                 135                 140

<210> SEQ ID NO 57
<211> LENGTH: 160
<212> TYPE: PRT
<213> ORGANISM: Haemophilus aegypticus

<400> SEQUENCE: 57

Met Lys Lys Ile Ile Leu Thr Leu Ser Leu Gly Leu Leu Thr Ala Cys
1               5                   10                  15

```
Ser Ala Gln Thr Gln Lys Ala Glu Gln Asn Asp Val Lys Leu Thr Pro
         20                  25                  30

Pro Thr Asp Val Arg Ser Gly Tyr Ile Arg Leu Val Lys Asn Val Asn
             35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
             115                 120                 125

Lys His Thr Leu Ser Leu Thr Pro Asp Thr Thr Leu Tyr Asn Ala Ala
         130                 135                 140

Gln Ile Ile Cys Ala Asn Tyr Gly Lys Ala Phe Ser Val Asp Lys Lys
145                 150                 155                 160

<210> SEQ ID NO 58
<211> LENGTH: 160
<212> TYPE: PRT
<213> ORGANISM: Haemophilus influenzae

<400> SEQUENCE: 58

Met Thr Lys Ile Ile Leu Thr Leu Ser Leu Gly Leu Leu Thr Ala Cys
1               5                   10                  15

Ser Ala Gln Thr Gln Lys Val Glu Gln Asn Asp Val Lys Leu Thr Ala
         20                  25                  30

Pro Thr Asp Val Arg Ser Gly Tyr Val Arg Leu Val Lys Asn Val Asn
             35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                 85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
             115                 120                 125

Lys His Thr Leu Ser Leu Thr Pro Asp Thr Thr Leu Tyr Asn Ala Ala
         130                 135                 140

Gln Ile Ile Cys Ala Asn Tyr Gly Lys Ala Phe Leu Val Asp Lys Lys
145                 150                 155                 160

<210> SEQ ID NO 59
<211> LENGTH: 126
<212> TYPE: PRT
<213> ORGANISM: Haemophilus influenzae

<400> SEQUENCE: 59

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
         20                  25                  30
```

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
                100                 105                 110

Asp Glu Phe Trp Gly Gln Gly Leu Tyr Val Lys Phe Asn Thr
                115                 120                 125

<210> SEQ ID NO 60
<211> LENGTH: 145
<212> TYPE: PRT
<213> ORGANISM: Haemophilus influenzae

<400> SEQUENCE: 60

Met Lys Lys Ile Ile Leu Thr Leu Ser Leu Gly Leu Leu Thr Ala Cys
 1               5                  10                  15

Ser Ala Gln Thr Gln Lys Val Glu Gln Asn Asp Val Lys Leu Thr Ala
                20                  25                  30

Pro Thr Asp Val Arg Ser Gly Tyr Val Arg Leu Val Lys Asn Val Asn
            35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
                100                 105                 110

Asp Glu Phe Trp Gly Gln Gly Leu Arg Ala Ala Pro Lys Lys Gln Lys
                115                 120                 125

Lys His Thr Leu Ser Leu Thr Pro Asp Thr Thr Leu Tyr Asn Ala Ala
                130                 135                 140

Gln
145

<210> SEQ ID NO 61
<211> LENGTH: 151
<212> TYPE: PRT
<213> ORGANISM: Haemophilus influenzae

<400> SEQUENCE: 61

Met Lys Lys Ile Ile Leu Thr Leu Ser Leu Gly Leu Leu Thr Ala Cys
 1               5                  10                  15

Ser Ala Gln Ile Gln Lys Ala Glu Gln Asn Asp Met Lys Leu Ala Pro
                20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
 50                  55                  60

Ile Val His Phe Asp Ala Val Val Asn Leu Asp Lys Gly Leu Tyr Val
 65                  70                  75                  80

```
Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr
145                 150

<210> SEQ ID NO 62
<211> LENGTH: 152
<212> TYPE: PRT
<213> ORGANISM: Haemophilus influenzae

<400> SEQUENCE: 62

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
                85                  90                  95

Leu Asn Cys Ala Asn Tyr His Leu Thr Gln Ile Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly
145                 150
```